(12) United States Patent
Smith et al.

(10) Patent No.: US 10,953,030 B2
(45) Date of Patent: Mar. 23, 2021

(54) 4'-FLUORO-2'-METHYL SUBSTITUTED NUCLEOSIDE DERIVATIVES AS INHIBITORS OF HCV RNA REPLICATION

(71) Applicant: RIBOSCIENCE LLC, Sunnyvale, CA (US)

(72) Inventors: Mark Smith, San Francisco, CA (US); Klaus G. Klumpp, Palo Alto, CA (US)

(73) Assignee: Riboscience LLC, Palo Alto, CA (US)

( * ) Notice: Subject to any disclaimer, the term of this patent is extended or adjusted under 35 U.S.C. 154(b) by 0 days.

(21) Appl. No.: 16/532,210

(22) Filed: Aug. 5, 2019

(65) Prior Publication Data

US 2020/0197431 A1    Jun. 25, 2020

Related U.S. Application Data

(63) Continuation of application No. 15/710,886, filed on Sep. 21, 2017, now abandoned, which is a continuation-in-part of application No. 14/278,990, filed on May 15, 2014, now Pat. No. 9,895,442.

(60) Provisional application No. 61/824,030, filed on May 16, 2013.

(51) Int. Cl.
| | |
|---|---|
| C07H 19/20 | (2006.01) |
| A61K 31/7072 | (2006.01) |
| A61K 31/7056 | (2006.01) |
| A61K 31/4709 | (2006.01) |
| A61K 31/4184 | (2006.01) |
| A61K 31/4188 | (2006.01) |
| A61K 45/06 | (2006.01) |
| A61P 1/16 | (2006.01) |
| A61K 31/4178 | (2006.01) |
| A61P 31/14 | (2006.01) |
| A61K 31/683 | (2006.01) |

(52) U.S. Cl.
CPC ...... *A61K 31/7072* (2013.01); *A61K 31/4178* (2013.01); *A61K 31/4184* (2013.01); *A61K 31/4188* (2013.01); *A61K 31/4709* (2013.01); *A61K 31/683* (2013.01); *A61K 31/7056* (2013.01); *A61K 45/06* (2013.01); *A61P 1/16* (2018.01); *A61P 31/14* (2018.01); *C07H 19/20* (2013.01); *A61K 2300/00* (2013.01)

(58) Field of Classification Search
None
See application file for complete search history.

(56) References Cited

U.S. PATENT DOCUMENTS

| | | |
|---|---|---|
| 4,147,864 A | 4/1979 | Woodward et al. |
| 5,807,876 A | 9/1998 | Armistead et al. |
| 6,054,472 A | 4/2000 | Armistead et al. |
| 6,344,465 B1 | 2/2002 | Armistead et al. |
| 6,498,178 B2 | 12/2002 | Stamos et al. |
| 7,429,572 B2 | 9/2008 | Clark |
| 7,964,580 B2 | 6/2011 | Sofia et al. |
| 8,173,621 B2 | 5/2012 | Du et al. |
| 8,334,270 B2 | 12/2012 | Sofia et al. |
| 8,415,322 B2 | 4/2013 | Clark |
| 8,580,765 B2 | 11/2013 | Sofia et al. |
| 8,735,372 B2 | 5/2014 | Du et al. |
| 8,759,510 B2 | 6/2014 | Du et al. |
| 2003/0170891 A1 | 9/2003 | McSwiggen |
| 2003/0175950 A1 | 9/2003 | McSwiggen |
| 2005/0020884 A1 | 1/2005 | Hart et al. |
| 2007/0042988 A1 | 2/2007 | Klumpp et al. |
| 2010/0016251 A1 | 1/2010 | Sofia et al. |

(Continued)

FOREIGN PATENT DOCUMENTS

| | | |
|---|---|---|
| BE | 875247 A | 10/1979 |
| CN | 101918425 A | 12/2010 |

(Continued)

OTHER PUBLICATIONS

Sofia et al., "Discovery of a β-D-2'-Deoxy-2'-α-fluoro-2'-β-C-methyluridine Nucleotide Prodrug (PSI-7977) for the Treatment of Hepatitis C Virus," J. Med. Chem., 53(19), pp. 7202-7218 (2010).

(Continued)

*Primary Examiner* — Traviss C McIntosh, III

(74) *Attorney, Agent, or Firm* — Mintz Levin Cohn Ferris Glovsky and Popeo, P.C.

(57) ABSTRACT

Cytidine nucleoside analogues of Formula I, wherein the variables are as described herein, in combination with uridine nucleoside analogues of Formula II, wherein the variables are as described herein,

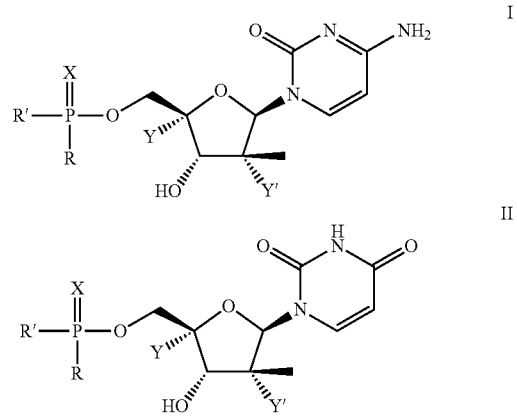

produce a synergistic effect on the inhibition of HCV polymerase.

15 Claims, No Drawings

(56) References Cited

U.S. PATENT DOCUMENTS

| | | |
|---|---|---|
| 2012/0232029 A1 | 9/2012 | Sofia et al. |
| 2012/0316327 A1 | 12/2012 | Chun et al. |
| 2013/0315867 A1 | 11/2013 | Parsy et al. |
| 2014/0178338 A1 | 6/2014 | Mayes et al. |
| 2014/0179627 A1* | 6/2014 | Beigelman ............... A61P 31/14 514/47 |

FOREIGN PATENT DOCUMENTS

| | | |
|---|---|---|
| CN | 102325783 A | 1/2012 |
| CN | 104011061 A | 8/2014 |
| CN | 105073766 A | 11/2015 |
| DE | 2506330 | 9/1975 |
| WO | WO-1986/006380 | 11/1986 |
| WO | WO-1997/040028 | 10/1997 |
| WO | WO-1998/017679 | 4/1998 |
| WO | WO-1998/022496 | 5/1998 |
| WO | WO-1998/040381 | 9/1998 |
| WO | WO-1999/001582 | 1/1999 |
| WO | WO-1999/007734 | 2/1999 |
| WO | WO-2000/006529 | 2/2000 |
| WO | WO-2000/009543 | 2/2000 |
| WO | WO-2000/010573 | 3/2000 |
| WO | WO-2000/013708 | 3/2000 |
| WO | WO-2000/018231 | 4/2000 |
| WO | WO-2000/056331 | 9/2000 |
| WO | WO-01/32153 | 5/2001 |
| WO | WO-2001/085172 | 11/2001 |
| WO | WO-2002/004425 | 1/2002 |
| WO | WO-2002/018369 | 3/2002 |
| WO | WO-2002/100846 | 12/2002 |
| WO | WO-2002/100851 | 12/2002 |
| WO | WO-03/000254 | 1/2003 |
| WO | WO-2003/007945 | 1/2003 |
| WO | WO-03/010141 | 2/2003 |
| WO | WO-2003/037893 | 5/2003 |
| WO | WO-2003/037894 | 5/2003 |
| WO | WO-2003/037895 | 5/2003 |
| WO | WO-2004/000858 | 12/2003 |
| WO | WO-2004/096235 | 11/2004 |
| WO | WO-2004/099241 | 11/2004 |
| WO | WO-2005/007810 | 1/2005 |
| WO | WO-2005/012327 | 2/2005 |
| WO | WO-2005/020884 | 3/2005 |
| WO | WO-2005/073195 | 8/2005 |
| WO | WO-2005/073216 | 8/2005 |
| WO | WO-2006/063281 | 6/2006 |
| WO | WO-2007/095269 | 8/2007 |
| WO | WO-2008/017507 | 2/2008 |
| WO | WO-2008/021927 | 2/2008 |
| WO | WO-2008/085508 | 7/2008 |
| WO | WO-2008/121634 | 10/2008 |
| WO | WO-2008/142055 | 11/2008 |
| WO | WO-2009/152095 | 12/2009 |
| WO | WO-2010/075554 | 7/2010 |
| WO | WO-2011/133871 | 10/2011 |
| WO | WO-2012/012465 | 1/2012 |
| WO | WO-2012/040127 | 3/2012 |
| WO | WO-2013/019874 | 2/2013 |
| WO | WO-2013/092481 | 6/2013 |
| WO | WO-2014/099941 | 6/2014 |
| WO | WO-2014/100505 | 6/2014 |
| WO | WO-2014/186637 | 11/2014 |

OTHER PUBLICATIONS

Clark et al., "Design, Synthesis, and Antiviral Activity of 2'-Deoxy-2'-fluoro-2'-C-methylcytidine, a Potent Inhibitor of Hepatitis C Virus Replication," J. Med. Chem., 48(17), pp. 5504-5508 (2005).

Congiatu et al., "Naphthyl phosphoramidate derivatives of BVdU as potential anticancer agents: design, synthesis and biological evaluation," Nucleosides, Nucleotides, and Nucleic Acids, 24(5-7), pp. 485-489 (2005).

Feng et al., "Role of Mitochondrial RNA Polymerase in the Toxicity of Nucleotide Inhibitors of Hepatitic C Virus," Antimicrobial Agents and Chemotherapy, 60, pp. 806-817 (2016).

Ma et al., "Characterization of the Metabolic Activation of Hepatitis C Virus Nucleoside Inhibitor β-D-2'-Deoxy-2'-fluoro-2'-C-methylcytidine (PSI-6130) and Identification of a Novel Active 5'-Triphosphate Species," The Journal of Biological Chemistry, JBC Papers in Press, 282:41, pp. 29812-29820 (2007).

McGuigan et al., "Phosphoramidate ProTides of 2'-C-Methylguanosine as Highly Potent Inhibitors of Hepatitis C Virus, Study of Their in Vitro and in Vivo Properties," J. Med. Chem., 53, pp. 4949-4957 (2010).

Sofia, "Chapter Two—Nucleotide Prodrugs for the Treatment of HCV Infection," Advances in Pharmacology, 67, pp. 39-73 (2013).

\* cited by examiner

4'-FLUORO-2'-METHYL SUBSTITUTED NUCLEOSIDE DERIVATIVES AS INHIBITORS OF HCV RNA REPLICATION

CROSS-REFERENCE TO RELATED APPLICATIONS

This application is a continuation of U.S. application Ser. No. 15/710,886 filed Sep. 21, 2017, which is a continuation-in-part of U.S. application Ser. No. 14/278,990 filed May 15, 2014 (now U.S. Pat. No. 9,895,442), which is an application claiming benefit under 35 U.S.C. § 119(e) of U.S. provisional application Ser. No. 61/824,030 filed May 16, 2013, the disclosures of which are incorporated herein by reference and are commonly owned.

FIELD OF THE INVENTION

The invention relates to combinations of nucleoside derivatives as inhibitors of HCV replicon RNA replication. In particular, the invention is concerned with the use of combinations of cytidine and uridine pyrimidine nucleoside derivatives as inhibitors of subgenomic hepatitis C virus (HCV) RNA replication and pharmaceutical compositions containing such compounds. In particular, the cytidine nucleoside analogues of Formula I, in combination with the uridine nucleoside analogues of Formula II, produce a synergistic effect on the inhibition of HCV polymerase.

BACKGROUND OF THE INVENTION

Hepatitis C virus is the leading cause of chronic liver disease throughout the world. Patients infected with HCV are at risk of developing cirrhosis of the liver and subsequent hepatocellular carcinoma and hence HCV is the major indication for liver transplantation. Only two approved therapies are currently available for the treatment of HCV infection (R. G. Gish, Sem. Liver. Dis., 1999, 19, 35). These are interferon-α monotherapy and, more recently, combination therapy of the nucleoside analogue, ribavirin (Virazole), with interferon-α.

Many of the drugs approved for the treatment of viral infections are nucleosides or nucleoside analogues and most of these nucleoside analogue drugs inhibit viral replication, following conversion to the corresponding triphosphates, through inhibition of the viral polymerase enzymes. This conversion to the triphosphate is commonly mediated by cellular kinases and therefore the direct evaluation of nucleosides as inhibitors of HCV replication is only conveniently carried out using a cell-based assay. For HCV the availability of a true cell-based viral replication assay or animal model of infection is lacking.

Hepatitis C virus belongs to the family of Flaviridae. It is an RNA virus, the RNA genome encoding a large polyprotein which after processing produces the necessary replication machinery to ensure synthesis of progeny RNA. It is believed that most of the non-structural proteins encoded by the HCV RNA genome are involved in RNA replication. Lohmann et al. [V. Lohmann et al., Science, 1999, 285, 110-113] have described the construction of a Human Hepatoma (Huh7) cell line in which subgenomic HCV RNA molecules have been introduced and shown to replicate with high efficiency. It is believed that the mechanism of RNA replication in these cell lines is identical to the replication of the full length HCV RNA genome in infected hepatocytes. The subgenomic HCV cDNA clones used for the isolation of these cell lines have formed the basis for the development of a cell-based assay for identifying nucleoside analogue inhibitors of HCV replication.

SUMMARY OF THE INVENTION

The application provides a compound of Formula I

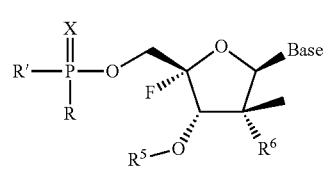

wherein:
R is O—$R^1$ or $NHR^{1'}$;
or R and $R^5$ together form a bond;
R' is $N(R^4)C(R^{2a})(R^{2b})C(=O)OR^3$ or —$OR^3$;
$R^1$ is H, lower haloalkyl, or aryl, wherein aryl is phenyl or naphthyl, optionally substituted with one or more lower alkyl, lower alkenyl, lower alkynyl, lower alkoxy, halo, lower haloalkyl, —$N(R^{1a})_2$, acylamino, —$SO_2N(R^{1a})_2$, —$COR^{1b}$, —$SO_2(R^{1c})$, —$NHSO_2(R^{1c})$, nitro or cyano;
each $R^{1a}$ is independently H or lower alkyl;
each $R^{1b}$ is independently —$OR^{1a}$ or —$N(R^{1a})_2$;
each $R^{1c}$ is lower alkyl;
$R^{1'}$ is —$C(R^{2a})(R^{2b})C(=O)OR^3$;
each $R^{2a}$ and $R^{2b}$ are independently H, lower alkyl, —$(CH_2)_rN(R^{1a})_2$, lower hydroxyalkyl, —$CH_2SH$, —$(CH_2)S(O)_pMe$, —$(CH_2)_3NHC(=NH)NH_2$, (1H-indol-3-yl)methyl, (1H-indol-4-yl)methyl, —$(CH2)_mC(=O)R^{1b}$, aryl and aryl lower alkyl, wherein aryl may optionally be substituted with one or more hydroxy, lower alkyl, lower alkoxy, halo, nitro or cyano;
or $R^{2a}$ is H and $R^{2b}$ and $R^4$ together form $(CH_2)_n$;
each $R^3$ is H, lower alkyl, lower haloalkyl, phenyl or phenyl lower alkyl;
each $R^4$ is H, lower alkyl, or $R^{2b}$ and $R^4$ together form $(CH_2)_3$;
$R^5$ is H, $C(=O)R^{1c}$, $C(=O)R^{1b}$, $P(=O)(OR^1)(OR^{1a})$, or $P(=O)(OR^1)(NR^4R^7)$;
$R^6$ is OH or F;
$R^7$ is $C(R^{2a}R^{2b})C(=O)OR^3$
m is 0 to 3;
n is 3, 4 or 5;
p is 0 to 2;
r is 1 to 6;
X is O or S; and
Base is uracil, cytosine, guanine, adenine, thymine, or heterocycloalkyl, each of which may optionally substituted with one or more hydroxy, lower alkyl, lower alkoxy, halo, nitro or cyano;
or a pharmacologically acceptable salt thereof.

The compounds of Formula I are useful for the treatment of diseases mediated by the hepatitis C virus (HCV) and for pharmaceutical compositions comprising such compounds.

The application provides a method for treating a hepatitis C virus (HCV) infection comprising administering to a patient in need thereof a therapeutically effective amount of a compound of Formula I.

The application provides a composition comprising a compound of Formula I and a pharmaceutically acceptable excipient.

DETAILED DESCRIPTION OF THE INVENTION

The compounds of Formulae I and II have been shown to be inhibitors of subgenomic hepatitis C virus replication in a hepatoma cell line. These compounds have the potential to be efficacious as antiviral drugs for the treatment of HCV infections in human.

Combination Therapy

The compounds of the invention and their isomeric forms and pharmaceutically acceptable salts thereof are useful in treating and preventing HCV infection alone or when used in combination with other compounds targeting viral or cellular elements or functions involved in the HCV lifecycle. Classes of compounds useful in the invention include, without limitation, all classes of HCV antivirals.

In particular, the cytidine nucleoside analogues of Formula I, in combination with the uridine nucleoside analogues of Formula II, produce a synergistic effect on the inhibition of HCV polymerase.

For combination therapies, mechanistic classes of agents that can be useful when combined with the compounds of the invention include, for example, nucleoside and non-nucleoside inhibitors of the HCV polymerase, protease inhibitors, helicase inhibitors, NS4B inhibitors and medicinal agents that functionally inhibit the internal ribosomal entry site (IRES) and other medicaments that inhibit HCV cell attachment or virus entry, HCV RNA translation, HCV RNA transcription, replication or HCV maturation, assembly or virus release. Specific compounds in these classes and useful in the invention include, but are not limited to, macrocyclic, heterocyclic and linear HCV protease inhibitors such as telaprevir (VX-950), boceprevir (SCH-503034), narlaprevir (SCH-9005 18), ITMN-191 (R-7227), TMC-435350 (a.k.a. TMC-435), MK-7009, BI-201335, BI-2061 (ciluprevir), BMS-650032, ACH-1625, ACH-1095 (HCV NS4A protease co-factor inhibitor), VX-500, VX-8 13, PHX-1766, PHX2054, IDX-136, IDX-3 16, ABT-450 EP-0 13420 (and congeners) and VBY-376; the Nucleosidic HCV polymerase (replicase) inhibitors useful in the invention include, but are not limited to, R7128, PSI-785 1, IDX-184, IDX-102, R1479, UNX-08 189, PSI-6130, PSI-938 and PSI-879 and various other nucleoside and nucleotide analogs and HCV inhibitors including (but not limited to) those derived as 2'-C-methyl modified nucleos(t)ides, 4'-aza modified nucleos(t)ides, and 7'-deaza modified nucleos(t)ides. Non-nucleosidic HCV polymerase (replicase) inhibitors useful in the invention, include, but are not limited to, HCV-796, HCV-371, VCH-759, VCH-916, VCH-222, ANA-598, MK-3281, ABT-333, ABT-072, PF-00868554, BI-207127, GS-9190, A-837093, JKT-109, GL-59728 and GL-60667.

In addition, compounds of the invention can be used in combination with cyclophyllin and immunophyllin antagonists (e.g., without limitation, DEBIO compounds, NM-811 as well as cyclosporine and its derivatives), kinase inhibitors, inhibitors of heat shock proteins (e.g., HSP90 and HSP70), other immunomodulatory agents that can include, without limitation, interferons (-alpha, -beta, -omega, -gamma, -lambda or synthetic) such as Intron A, Roferon-A, Canferon-A300, Advaferon, Infergen, Humoferon, Sumiferon MP, Alfaferone, IFN-β, Feron and the like; polyethylene glycol derivatized (pegylated) interferon compounds, such as PEG interferon-α-2a (Pegasys), PEG interferon-α-2b (PEGIntron), pegylated IFN-α-con1 and the like; long acting formulations and derivatizations of interferon compounds such as the albumin-fused interferon, Albuferon, Locteron, and the like; interferons with various types of controlled delivery systems (e.g., ITCA-638, omega-interferon delivered by the DUROS subcutaneous delivery system); compounds that stimulate the synthesis of interferon in cells, such as resiquimod and the like; interleukins; compounds that enhance the development of type 1 helper T cell response, such as SCV-07 and the like; TOLL-like receptor agonists such as CpG-10101 (actilon), isotorabine, ANA773 and the like; thymosin α-1; ANA-245 and ANA-246; histamine dihydrochloride; propagermanium; tetrachlorodecaoxide; ampligen; IMP-321; KRN-7000; antibodies, such as civacir, XTL-6865 and the like and prophylactic and therapeutic vaccines such as InnoVac C, HCV E1E2/MF59 and the like. In addition, any of the above-described methods involving administering an NS5A inhibitor, a Type I interferon receptor agonist (e.g., an IFN-α) and a Type II interferon receptor agonist (e.g., an IFN-γ) can be augmented by administration of an effective amount of a TNF-α antagonist. Exemplary, non-limiting TNF-α antagonists that are suitable for use in such combination therapies include ENBREL, REMICADE, and HUMIRA.

In addition, compounds of the invention can be used in combination with antiprotozoans and other antivirals thought to be effective in the treatment of HCV infection such as, without limitation, the prodrug nitazoxanide. Nitazoxanide can be used as an agent in combination with the compounds disclosed in this invention as well as in combination with other agents useful in treating HCV infection such as peginterferon α-2a and ribavirin.

Compounds of the invention can also be used with alternative forms of interferons and pegylated interferons, ribavirin or its analogs (e.g., tarabavarin, levoviron), microRNA, small interfering RNA compounds (e.g., SIRPLEX-140-N and the like), nucleotide or nucleoside analogs, immunoglobulins, hepatoprotectants, anti-inflammatory agents and other inhibitors of NS5A. Inhibitors of other targets in the HCV lifecycle include NS3 helicase inhibitors; NS4A co-factor inhibitors; antisense oligonucleotide inhibitors, such as ISIS-14803, AVI-4065 and the like; vector-encoded short hairpin RNA (shRNA); HCV specific ribozymes such as heptazyme, RPI, 13919 and the like; entry inhibitors such as HepeX-C, HuMax-HepC and the like; alpha glucosidase inhibitors such as celgosivir, UT-231B and the like; KPE-02003002 and BIVN 401 and IMPDH inhibitors. Other illustrative HCV inhibitor compounds include those disclosed in the following publications: U.S. Pat. Nos. 5,807,876; 6,498,178; 6,344,465; and 6,054,472; PCT Patent Application Publication Nos. WO97/40028; WO98/4038 1; WO00/56331, WO02/04425; WO03/007945; WO03/010141; WO03/000254; WO01/32153; WO00/06529; WO00/18231; WO00/10573; WO00/13708; WO01/85172; WO03/037893; WO03/037894; WO03/037895; WO02/100851; WO02/100846; WO99/01582; WO00/09543; WO02/18369; WO98/17679, WO00/056331; WO98/22496; WO99/07734; WO05/073216, WO05/073195 and WO08/021927.

Additionally, combinations of, for example, ribavirin and interferon, may be administered as multiple combination therapy with at least one of the compounds of the invention. The present invention is not limited to the aforementioned classes or compounds and contemplates known and new compounds and combinations of biologically active agents. It is intended that combination therapies of the present invention include any chemically compatible combination of a compound of this inventive group with other compounds of the inventive group or other compounds outside of the inventive group, as long as the combination does not eliminate the anti-viral activity of the compound of this inventive group or the anti-viral activity of the pharmaceutical composition itself.

Combination therapy can be sequential, that is treatment with one agent first and then a second agent (for example, where each treatment comprises a different compound of the invention or where one treatment comprises a compound of the invention and the other comprises one or more biologically active agents) or it can be treatment with both agents at the same time (concurrently). Sequential therapy can include a reasonable time after the completion of the first therapy before beginning the second therapy. Treatment with both agents at the same time can be in the same daily dose or in separate doses. Combination therapy need not be limited to two agents and may include three or more agents. The dosages for both concurrent and sequential combination therapy will depend on absorption, distribution, metabolism and excretion rates of the components of the combination therapy as well as other factors known to one of skill in the art. Dosage values will also vary with the severity of the condition to be alleviated. It is to be further understood that for any particular subject, specific dosage regimens and schedules may be adjusted over time according to the individual's need and the judgment of the one skilled in the art administering or supervising the administration of the combination therapy.

The application provides a method for treating a hepatitis C virus (HCV) infection comprising administering to a patient in need thereof a therapeutically effective amount of a compound of any one of Formula I.

The application provides the above method, further comprising administering an immune system modulator or an antiviral agent that inhibits replication of HCV, or a combination thereof.

The application provides the above method, wherein the immune system modulator is an interferon or chemically derivatized interferon.

The application provides the above methods, wherein the antiviral agent is selected from the group consisting of a HCV protease inhibitor, a HCV polymerase inhibitor, a HCV helicase inhibitor, a HCV primase inhibitor, a HCV fusion inhibitor, and a combination thereof.

It will be understood that references herein to treatment extend to prophylaxis as well as to the treatment of existing conditions, and that the treatment of animals includes the treatment of humans as well as other mammals. Furthermore, treatment of an hepatitis C virus (HCV) infection, as used herein, also includes treatment or prophylaxis of a disease or a condition associated with or mediated by hepatitis C virus (HCV) infection, or the clinical symptoms thereof.

The term "alkyl" as used herein denotes a straight or branched chain hydrocarbon residue containing 1 to 12 carbon atoms. Preferably, the term "alkyl" denotes a straight or branched chain hydrocarbon residue containing 1 to 7 carbon atoms. Most preferred are methyl, ethyl, propyl, isopropyl, n-butyl, isobutyl, tert -butyl or pentyl. The alkyl may be unsubstituted or substituted. The substituents are selected from one or more of cycloalkyl, nitro, amino, alkyl amino, dialkyl amino, alkyl carbonyl and cycloalkyl carbonyl.

The term "cycloalkyl" as used herein denotes an optionally substituted cycloalkyl group containing 3 to 7 carbon atoms, e. g. cyclopropyl, cyclobutyl, cyclopentyl, cyclohexyl or cycloheptyl.

The term "alkoxy" as used herein denotes an optionally substituted straight or branched chain alkyl-oxy group wherein the "alkyl" portion is as defined above such as methoxy, ethoxy, n-propyloxy, i-propyloxy, n-butyloxy, i-butyloxy, tert. -butyloxy, pentyloxy, hexyloxy, heptyloxy including their isomers.

The term "alkoxyalkyl" as used herein denotes an alkoxy group as defined above which is bonded to an alkyl group as defined above. Examples are methoxymethyl, methoxyethyl, methoxypropyl, ethoxymethyl, ethoxyethyl, ethoxypropyl, propyloxypropyl, methoxybutyl, ethoxybutyl, propyloxybutyl, butyloxybutyl, tert. -butyloxybutyl, methoxypentyl, ethoxypentyl, propyloxypentyl including their isomers.

The term "alkenyl" as used herein denotes an unsubstituted or substituted hydrocarbon chain radical having from 2 to 7 carbon atoms, preferably from 2 to 4 carbon atoms, and having one or two olefinic double bonds, preferably one olefinic double bond. Examples are vinyl, 1-propenyl, 2-propenyl (allyl) or 2-butenyl (crotyl).

The term "alkynyl" as used herein denotes to unsubstituted or substituted hydrocarbon chain radical having from 2 to 7 carbon atoms, preferably 2 to 4 carbon atoms, and having one or where possible two triple bonds, preferably one triple bond. Examples are ethynyl, 1-propynyl, 2-propynyl, 1-butynyl, 2-butynyl or 3-butynyl.

The term "hydroxyalkyl" as used herein denotes a straight or branched chain alkyl group as defined above wherein 1, 2, 3 or more hydrogen atoms are substituted by a hydroxy group. Examples are hydroxymethyl, 1-hydroxyethyl, 2-hydroxyethyl, 1-hydroxypropyl, 2-hydroxypropyl, 3-hydroxypropyl, hydroxyisopropyl, hydroxybutyl and the like.

The term "haloalkyl" as used herein denotes a straight or branched chain alkyl group as defined above wherein 1, 2, 3 or more hydrogen atoms are substituted by a halogen. Examples are 1-fluoromethyl, 1-chloromethyl, 1-bromomethyl, 1-iodomethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl and the like.

The term "alkylthio" as used herein denotes a straight or branched chain (alkyl)S-group wherein the "alkyl" portion is as defined above. Examples are methylthio, ethylthio, n-propylthio, i-propylthio, n-butylthio, i-butylthio or tert.-butylthio.

The term "aryl" as used herein denotes an optionally substituted phenyl and naphthyl (e. g. 1-naphthyl, 2-naphthyl or 3-naphthyl). Suitable substituents for aryl can be selected from those named for alkyl, in addition however, halogen, hydroxy and optionally substituted alkyl, haloalkyl, alkenyl, alkynyl and aryloxy are substituents which can be added to the selection.

The term "heterocyclyl" as used herein denotes an optionally substituted saturated, partially unsaturated or aromatic monocyclic, bicyclic or tricyclic heterocyclic systems which contain one or more hetero atoms selected from nitrogen, oxygen and sulfur which can also be fused to an optionally substituted saturated, partially unsaturated or aromatic monocyclic carbocycle or heterocycle.

Examples of suitable heterocycles are oxazolyl, isoxazolyl, furyl, tetrahydrofuryl, 1,3-dioxolanyl, dihydropyranyl, 2-thienyl, 3-thienyl, pyrazinyl, isothiazolyl, dihydrooxazolyl, pyrimidinyl, tetrazolyl, 1-pyrrolidinyl, 2-pyrrolidinyl, 3-pyrrolidinyl, pyrrolidinonyl, (N-oxide)-pyridinyl, 1-pyrrolyl, 2-pyrrolyl, triazolyl e. g. 1,2,3-triazolyl or 1,2,4-triazolyl, 1-pyrazolyl, 2-pyrazolyl, 4-pyrazolyl, piperidinyl, morpholinyl (e. g. 4-morpholinyl), thiomorpholinyl (e. g. 4-thiomorpholinyl), thiazolyl, pyridinyl, dihydrothiazolyl, imidazolidinyl, pyrazolinyl, piperazinyl, 1-imidazolyl, 2-imidazolyl, 4-imidazolyl, thiadiazolyl e. g. 1,2,3-thiadiazolyl, 4-methylpiperazinyl, 4-hydroxypiperidin-1-yl.

Suitable substituents for heterocyclyl can be selected from those named for alkyl, in addition however, optionally substituted alkyl, alkenyl, alkynyl, an oxo group (═O) or aminosulphonyl are substituents which can be added to the selection.

The term "acyl" ("alkylcarbonyl") as used herein denotes a group of formula C(═O)R wherein R is hydrogen, an unsubstituted or substituted straight or branched chain hydrocarbon residue containing 1 to 7 carbon atoms or a phenyl group. Most preferred acyl groups are those wherein R is hydrogen, an unsubstituted straight chain or branched hydrocarbon residue containing 1 to 4 carbon atoms or a phenyl group.

The term halogen stands for fluorine, chlorine, bromine or iodine, preferable fluorine, chlorine, bromine.

In the pictorial representation of the compounds given throughout this application, a thickened tapered line (▬) indicates a substituent which is above the plane of the ring to which the asymmetric carbon belongs and a dotted line (⋯⋯) indicates a substituent which is below the plane of the ring to which the asymmetric carbon belongs.

Compounds of Formula I exhibit stereoisomerism. These compounds can be any isomer of the compound of Formula I or mixtures of these isomers. The compounds and intermediates of the present invention having one or more asymmetric carbon atoms may be obtained as racemic mixtures of stereoisomers which can be resolved.

Compounds of Formula I exhibit tautomerism that means that the compounds of this invention can exist as two or more chemical compounds that are capable of facile interconversion. In many cases it merely means the exchange of a hydrogen atom between two other atoms, to either of which it forms a covalent bond. Tautomeric compounds exist in a mobile equilibrium with each other, so that attempts to prepare the separate substances usually result in the formation of a mixture that shows all the chemical and physical properties to be expected on the basis of the structures of the components.

The most common type of tautomerism is that involving carbonyl, or keto, compounds and unsaturated hydroxyl compounds, or enols. The structural change is the shift of a hydrogen atom between atoms of carbon and oxygen, with the rearrangement of bonds. For example, in many aliphatic aldehydes and ketones, such as acetaldehyde, the keto form is the predominant one; in phenols, the enol form is the major component.

Compounds of Formula I which are basic can form pharmaceutically acceptable salts with inorganic acids such as hydrohalic acids (e.g. hydrochloric acid and hydrobromic acid), sulphuric acid, nitric acid and phosphoric acid, and the like, and with organic acids (e.g. with acetic acid, tartaric acid, succinic acid, fumaric acid, maleic acid, malic acid, salicylic acid, citric acid, methanesulphonic acid and p-toluene sulphonic acid, and the like). The formation and isolation of such salts can be carried out according to methods known in the art.

Inhibitors of HCV

The application provides a method of treatment of HCV by administering to a patient in need thereof a combination of a compound of Formula I in and a compound of Formula II

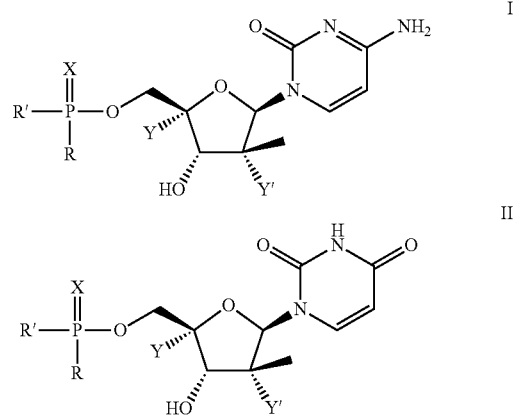

wherein:
each R is independently O—$R^1$ or NHC($R^{2a}$)($R^{2b}$)C(═O) O$R^3$;
each R' is independently O—$R^1$ or NHC($R^{2a}$)($R^{2b}$)C (═O)O$R^3$;
each $R^1$ is independently phenyl or naphthyl, optionally substituted with one or more lower alkyl, lower alkoxy, halo, lower haloalkyl, or cyano;
each $R^{2a}$ and $R^{2b}$ are independently H or lower alkyl;
each $R^3$ is independently H, lower alkyl, lower haloalkyl, phenyl or phenyl lower alkyl;
each X is independently O or S;
each Y is independently H or F; and
each Y' is independently F or OH;
or a pharmacologically acceptable salt thereof.

The application provides a method of treatment of HCV by administering to a patient in need thereof a combination of a compound of Formula I in and a compound of Formula II wherein Formula I is

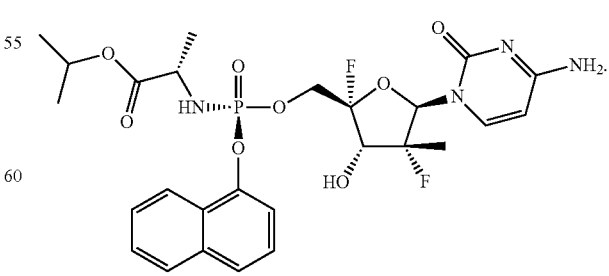

The application provides a method of treatment of HCV by administering to a patient in need thereof a combination of a compound of Formula I in and a compound of Formula II wherein Formula I is

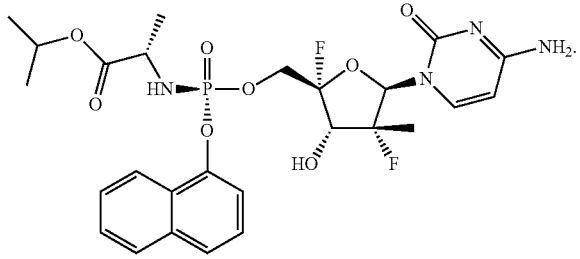 [SMILES: CC(C)OC(=O)[C@H](C)N[P@@](=O)(OC[C@@]1(F)O[C@@H](n2ccc(N)nc2=O)[C@](C)(F)[C@@H]1O)Oc1cccc2ccccc12]

The application provides a method of treatment of HCV by administering to a patient in need thereof a combination of a compound of Formula I in and a compound of Formula II wherein Formula I is

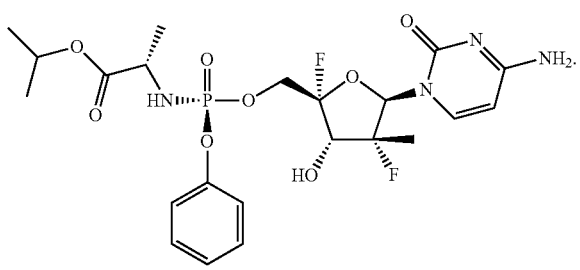 [SMILES: CC(C)OC(=O)[C@H](C)N[P@](=O)(OC[C@@]1(F)O[C@@H](n2ccc(N)nc2=O)[C@](C)(F)[C@@H]1O)Oc1ccccc1]

The application provides a method of treatment of HCV by administering to a patient in need thereof a combination of a compound of Formula I in and a compound of Formula II wherein Formula I is

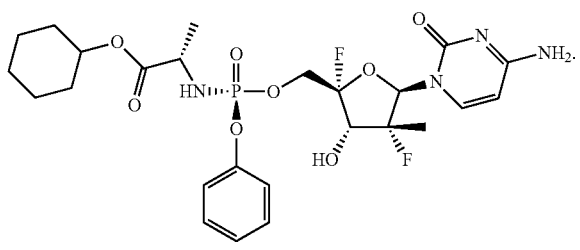 [SMILES: C[C@H](N[P@](=O)(OC[C@@]1(F)O[C@@H](n2ccc(N)nc2=O)[C@](C)(F)[C@@H]1O)Oc1ccccc1)C(=O)OC1CCCCC1]

The application provides a method of treatment of HCV by administering to a patient in need thereof a combination of a compound of Formula I in and a compound of Formula II wherein Formula I is

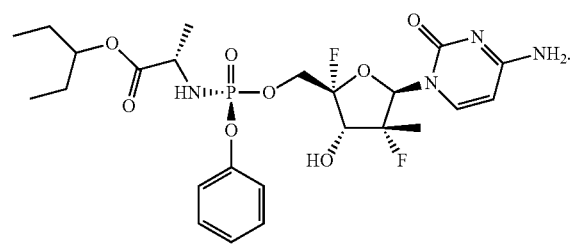 [SMILES: CCC(CC)OC(=O)[C@H](C)N[P@](=O)(OC[C@@]1(F)O[C@@H](n2ccc(N)nc2=O)[C@](C)(F)[C@@H]1O)Oc1ccccc1]

The application provides a method of treatment of HCV by administering to a patient in need thereof a combination of a compound of Formula I in and a compound of Formula II wherein Formula I is

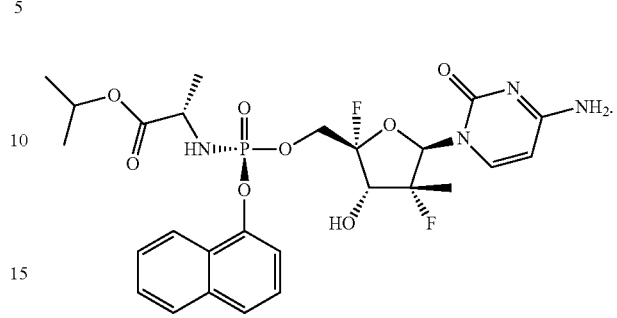

The application provides a method of treatment of HCV by administering to a patient in need thereof a combination of a compound of Formula I in and a compound of Formula II wherein Formula I is

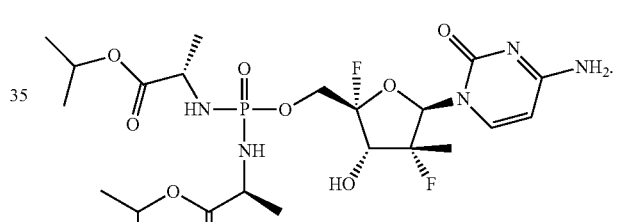

The application provides a method of treatment of HCV by administering to a patient in need thereof a combination of a compound of Formula I in and a compound of Formula II wherein Formula I is

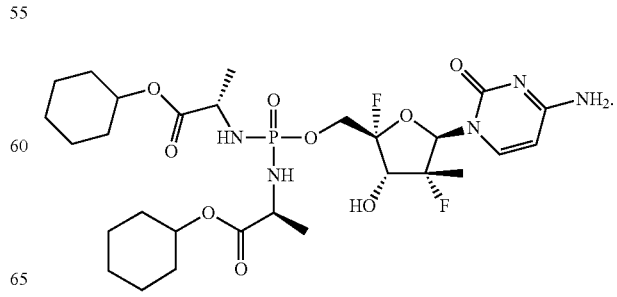

The application provides a method of treatment of HCV by administering to a patient in need thereof a combination of a compound of Formula I in and a compound of Formula II wherein Formula I is

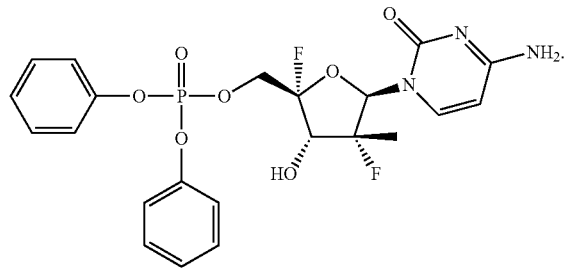 [SMILES: C[C@]1(F)[C@H](n2ccc(N)nc2=O)O[C@](F)(COP(=O)(Oc2ccccc2)Oc2ccccc2)[C@H]1O]

The application provides a method of treatment of HCV by administering to a patient in need thereof a combination of a compound of Formula I in and a compound of Formula II wherein Formula I is

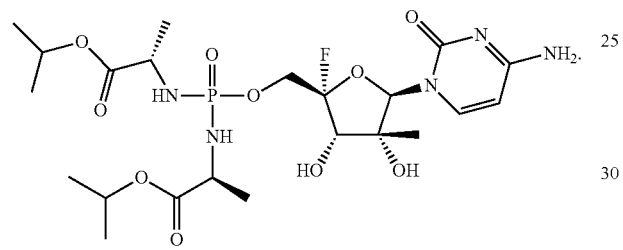

The application provides a method of treatment of HCV by administering to a patient in need thereof a combination of a compound of Formula I in and a compound of Formula II wherein Formula I is

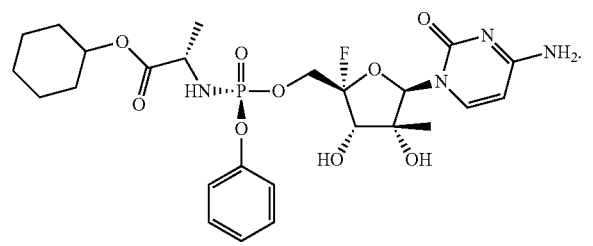 [SMILES: C[C@H](N[P@](=O)(OC[C@@]1(F)O[C@@H](n2ccc(N)nc2=O)[C@](C)(O)[C@@H]1O)Oc1ccccc1)C(=O)OC1CCCCC1]

The application provides a method of treatment of HCV by administering to a patient in need thereof a combination of a compound of Formula I in and a compound of Formula II wherein Formula I is

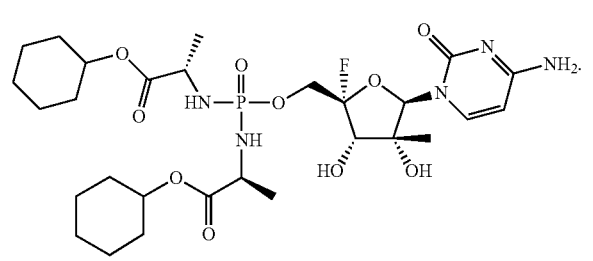 [SMILES: C[C@H](NP(=O)(N[C@@H](C)C(=O)OC1CCCCC1)OC[C@@]1(F)O[C@@H](n2ccc(N)nc2=O)[C@](C)(O)[C@@H]1O)C(=O)OC1CCCCC1]

The application provides a method of treatment of HCV by administering to a patient in need thereof a combination of a compound of Formula I in and a compound of Formula II wherein Formula I is

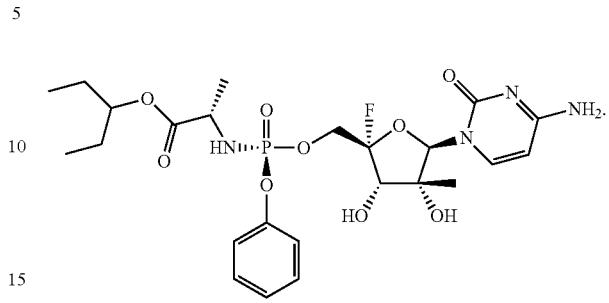

The application provides a method of treatment of HCV by administering to a patient in need thereof a combination of a compound of Formula I in and a compound of Formula II wherein Formula I is

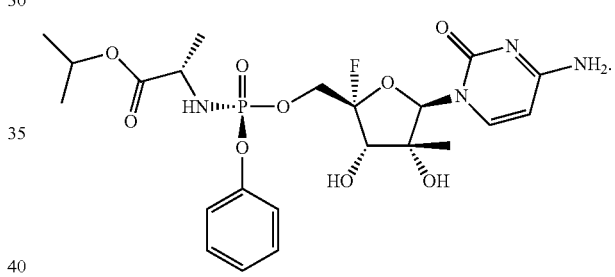

The application provides a method of treatment of HCV by administering to a patient in need thereof a combination of a compound of Formula I in and a compound of Formula II wherein Formula I is

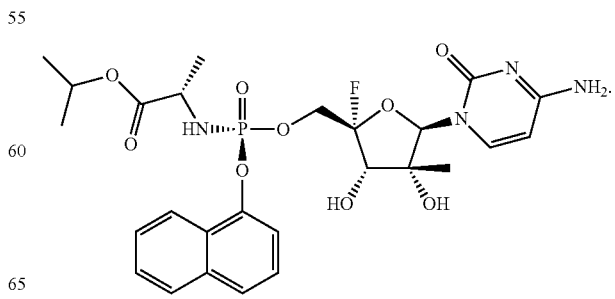

The application provides a method of treatment of HCV by administering to a patient in need thereof a combination of a compound of Formula I in and a compound of Formula II wherein Formula I is

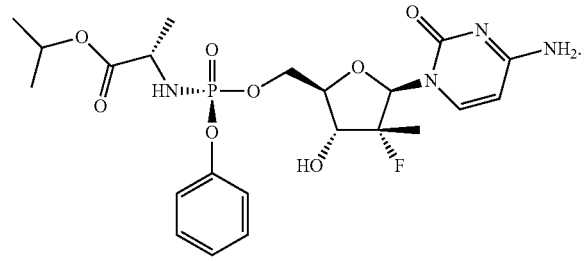 [SMILES: CC(C)OC(=O)[C@H](C)N[P@](=O)(OC[C@H]1O[C@@H](n2ccc(N)nc2=O)[C@](C)(F)[C@@H]1O)Oc1ccccc1]

The application provides a method of treatment of HCV by administering to a patient in need thereof a combination of a compound of Formula I in and a compound of Formula II wherein the compound of Formula II is Sofosbuvir

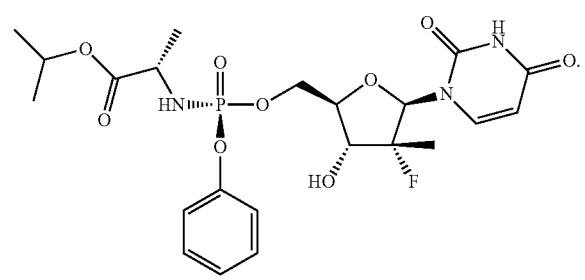 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]

The application provides a method of treatment of HCV by administering to a patient in need thereof a combination of a compound of Formula I in and a compound of Formula II wherein Formula II is

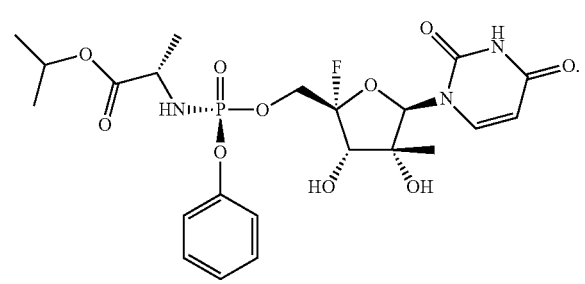 [SMILES: CC(C)OC(=O)[C@H](C)N[P@](=O)(OC[C@@]1(F)O[C@@H](n2ccc(=O)[nH]c2=O)[C@](C)(O)[C@@H]1O)Oc1ccccc1]

The application provides a method of treatment of HCV by administering to a patient in need thereof a combination of a compound of Formula I in and a compound of Formula II wherein compound of Formula II is

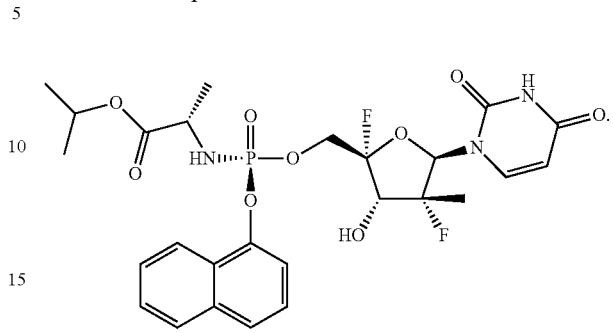

The application provides a method of treatment of HCV by administering to a patient in need thereof a combination of a compound of Formula I in and a compound of Formula II wherein compound of Formula II is

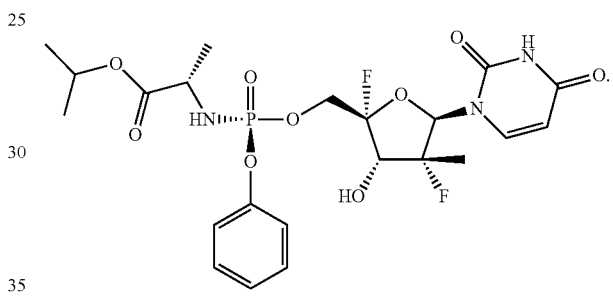

The application provides a method of treatment of HCV by administering to a patient in need thereof a combination of a compound of Formula I in and a compound of Formula II wherein the compound of Formula I and the compound of Formula II are, respectively,

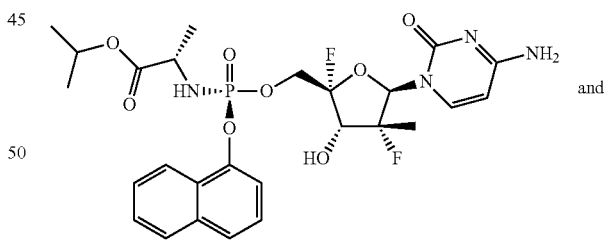

and

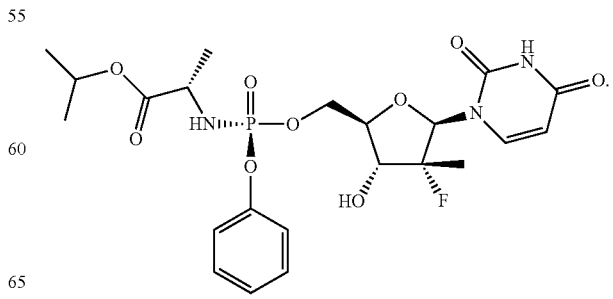

The application provides a method of treatment of HCV by administering to a patient in need thereof a combination of a compound of Formula I in and a compound of Formula II wherein the compound of Formula I and the compound of Formula II are, respectively,

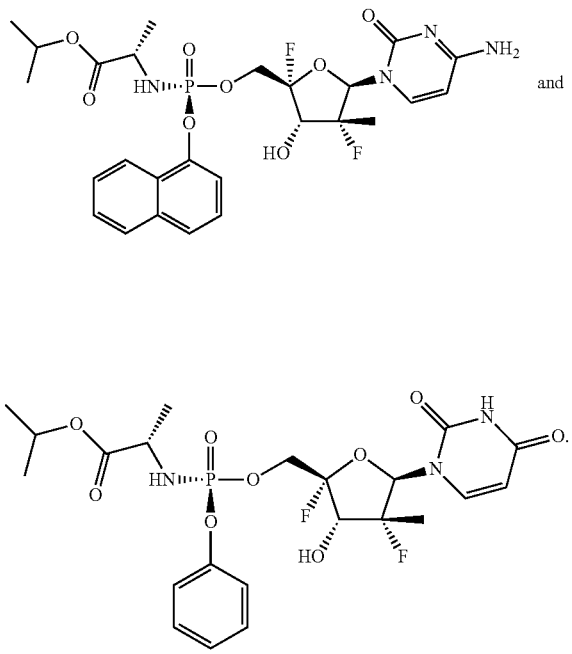

The application provides a method of treatment of HCV by administering to a patient in need thereof a combination of a compound of Formula I in and a compound of Formula II wherein the compound of Formula I and the compound of Formula II are, respectively,

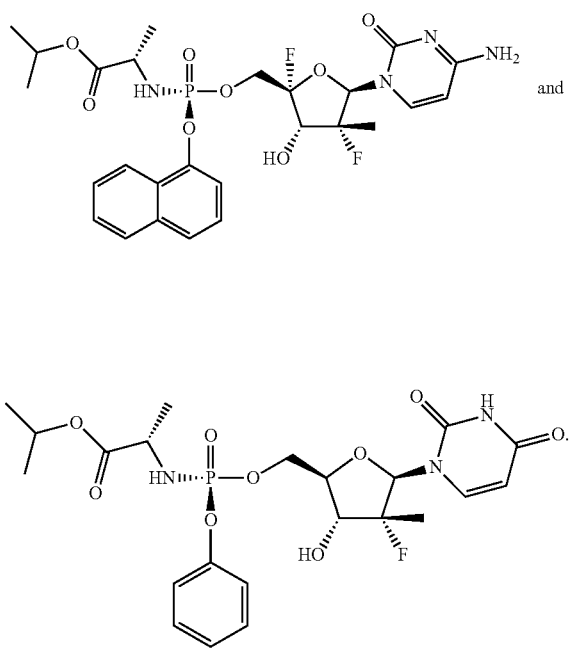

The application provides method of treatment of HCV by administering to a patient in need thereof a combination of a compound of Formula I in and a compound of Formula II wherein the compound of Formula I and the compound of Formula II are, respectively,

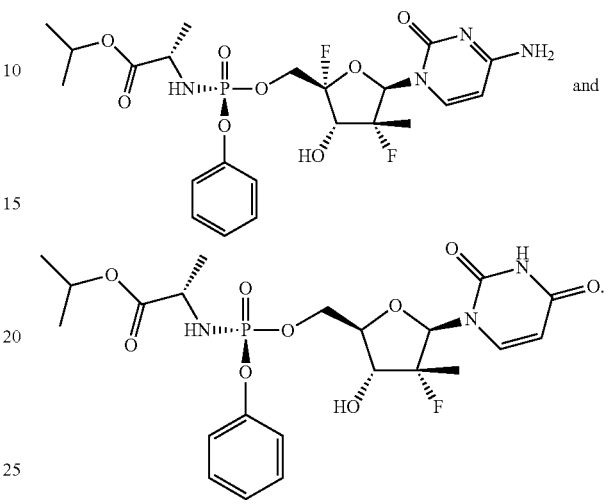

The application provides a method of treatment of HCV by administering to a patient in need thereof a combination of a compound of Formula I in and a compound of Formula II wherein the compound of Formula I is selected from the group consisting of:

(S)-2-{[(2S,3 S,4R,5R)-5-(2,4-Dioxo-3,4-dihydro-2H-pyrimidin-1-yl)-2,4-difluoro-3-hydroxy-4-methyl- tetrahydrofuran-2-ylmethoxy]-phenoxy-phosphorylamino}-propionic acid isopropyl ester;

(S)-2-[[(2S,3 S,4R,5R)-5-(2,4-Dioxo-3,4-dihydro-2H-pyrimidin-1-yl)-2,4-difluoro-3-hydroxy-4-methyl-tetrahydrofuran-2-ylmethoxy]-(naphthalen-1-yloxy)-phosphorylamino]-propionic acid isopropyl ester;

(S)-2-[[(2S,3S,4R,5R)-5-(2,4-Dioxo-3,4-dihydro-2H-pyrimidin-1-yl)-2,4-difluoro-3-hydroxy-4-methyl-tetrahydrofuran-2-ylmethoxy]-(naphthalen-2-yloxy)-phosphorylamino]-propionic acid isopropyl ester;

(S)-2-[[(2S,3S,4R,5R)-5-(2,4-dioxo-3,4-dihydro-2H-pyrimidin-1-yl)-2,4-difluoro-3-[((S)-1-isopropoxycarbonyl-ethylamino)-(naphthalen-2-yloxy)-phosphoryloxy]-4-methyl-tetrahydro-furan-2-ylmethoxy]-(naphthalen-2-yloxy)-phosphorylamino]-propionicacid isopropyl ester;

(S)-2-[[(2S,3S,4R,5R)-5-(2,4-Dioxo-3,4-dihydro-2H-pyrimidin-1-yl)-2,4-difluoro-4-methyl-3-propionyloxy- tetrahydro-furan-2-ylmethoxy]-(naphthalen-1-yl oxy)-phosphorylamino]-propionic acid isopropyl ester;

(S)-2-[(S)-[(2S,3S,4R,5R)-5-(2,4-Dioxo-3,4-dihydro-2H-pyrimidin-1-yl)-2,4-difluoro-3-hydroxy-4-methyl- tetrahydro-furan-2-ylmethoxy]-(naphthalen-2-yloxy)-phosphorylamino]-propionic acid isopropyl ester;

(S)-2-[(R)-[(2S,3S,4R,5R)-5-(2,4-Dioxo-3,4-dihydro-2H-pyrimidin-1-yl)-2,4-difluoro-3-hydroxy-4-methyl- tetrahydro-furan-2-ylmethoxy]-(naphthalen-2-yloxy)-phosphorylamino]-propionic acid isopropyl ester;

(S)-2-[(R)-[(2S,3S,4R,5R)-5-(2,4-Dioxo-3,4-dihydro-2H-pyrimidin-1-yl)-2,4-difluoro-3-hydroxy-4-methyl- tetrahydro-furan-2-ylmethoxy]-(naphthalen-1-yloxy)-phosphorylamino]-propionic acid isopropyl ester;

(S)-2-[(S)-[(2S,3S,4R,5R)-5-(2,4-Dioxo-3,4-dihydro-2H-pyrimidin-1-yl)-2,4-difluoro-3-hydroxy-4-methyl-tetrahydro-furan-2-ylmethoxy]-(naphthalen-1-yloxy)-phosphorylamino]-propionic acid isopropyl ester;
(S)-2-{(S)-[(2S,3S,4R,5R)-5-(2,4-Dioxo-3,4-dihydro-2H-pyrimidin-1-yl)-2,4-difluoro-3-hydroxy-4-methyl-tetrahydro-furan-2-ylmethoxy}-phenoxy-phosphorylamino]-propionic acid isopropyl ester;
(S)-2-{(R)-[(2S,3S,4R, 5R)-5-(2,4-Dioxo-3,4-dihydro-2H-pyrimidin-1-yl)-2,4-difluoro-3-hydroxy-4-methyl-tetrahydro-furan-2-ylmethoxy]-phenoxy-phosphorylamino}-propionic acid isopropyl ester;
(S)-2-[(S)-[(2S,3S,4R, 5R)-5-(5-Bromo-2,4-dioxo-3,4-dihydro-2H-pyrimidin-1-yl)-2,4-difluoro-3-hydroxy-4-methyl-tetrahydro-furan-2-ylmethoxy]-(naphthalen-1-yloxy)-phosphorylamino]-propionic acid isopropyl ester;
(S)-2-[(S)-[(2S,3 S,4R,5R)-5-(5-Bromo-2,4-dioxo-3,4-dihydro-2H-pyrimidin-1-yl)-2,4-difluoro-3-hydroxy-4-methyl-tetrahydro-furan-2-ylmethoxy]-(naphthalen-2-yloxy)-phosphorylamino]-propionic acid isopropyl ester;
(S)-2-[(R)-[(2S,3 S,4R,5R)-5-(5-Bromo-2,4-dioxo-3,4-dihydro-2H-pyrimidin-1-yl)-2,4-difluoro-3-hydroxy-4-methyl-tetrahydro-furan-2-ylmethoxy]-(naphthalen-1-yloxy)-phosphorylamino]-propionic acid isopropyl ester;
(S)-2-[(R)-[(2S,3 S,4R,5R)-5-(5-Bromo-2,4-dioxo-3,4-dihydro-2H-pyrimidin-1-yl)-2,4-difluoro-3-hydroxy-4-methyl-tetrahydro-furan-2-ylmethoxy]-(naphthalen-2-yloxy)-phosphorylamino]-propionic acid isopropyl ester; and
(S)-2-[[(2S,3 S,4R,5R)-5-(5-Bromo-2,4-dioxo-3,4-dihydro-2H-pyrimidin-1-yl)-2,4-difluoro-3-hydroxy-4- methyl-tetrahydro-furan-2-ylmethoxy]-(naphthalen-2-yloxy)-phosphorylamino]-propionic acid isopropyl ester.

The application provides a method of treatment of HCV by administering to a patient in need thereof a combination of a compound of Formula I in and a compound of Formula II wherein the compound of Formula I is selected from the group consisting of:
2'-Deoxy-2',4'-difluoro-2'-methycytidine-5'-(O-phenyl-N-(S)-1-(isopropoxycarbonyl)ethyl thiophosphoramidate;
2'-Deoxy-2',4'-difluoro-2'-methylcytidine-5'-(O-1-naphthyl-N-(S)-1-(isopropoxycarbonyl)ethyl thiosphosphoramidate;
2'-Deoxy-2',4'-difluoro-2'-methylcytidine-5'-(O-2-naphthyl-N-(S)-1-(isopropoxycarbonyl)ethyl thiosphosphoramidate;
2'-Deoxy-2',4'-difluoro-2'-methylcytidine-3',5'-cyclic phosphoric acid isopropyl ester;
2'-Deoxy-2',4'-difluoro-2'-methylcytidine-3',5'-cyclic thiophosphoric acid isopropyl ester;
4'-Fluoro-2'-methylcytidine-5'-(O-phenyl-N-(S)-1-(isopropoxycarbonyl)ethyl phosphoramidate;
4'-Fluoro-2'-cytidine-5'-(O-1-naphthyl-N-(S)-1-(isopropoxycarbonyl)ethyl phosphoramidate;
4'-Fluoro-2'-methylcytidine-5'-(O-1-naphthyl-N-(S)-2-(isopropoxycarbonyl)ethyl phosphoramidate;
4'-Fluoro-2'-methylcytidine-5'-(O-phenyl-N-(S)-1-(isopropoxycarbonyl)ethyl thiophsphoramidate;
4'-Fluoro-2'-methylcytidine-5'-(O-1-naphthyl-N-(S)-1-(isopropoxycarbonyl)ethyl thiophosphoramidate;
4'-Fluoro-2'-methylcytidine-5'-(O-1-naphthyl-N-(S)-2-(isopropoxycarbonyl)ethyl thiophosphoramidate;
4'-Fluoro-2'-methylcytidine-3',5'-cyclic phosphoric acid isopropyl ester;
4'-Fluoro-2'-methylcytidine-3',5'-cyclic thiophosphoric acid isopropyl ester;
2'-Deoxy-2',4'-difluoro-2'-methylcytidine-5'-{N,N'-bis[(S)-1-(isopropoxylcarbonyl)ethyl]phosphorodiamidate;
2'-Deoxy-2',4'-difluoro-2'-methylcytidine-5'-{N,N'-bis[(S)-1-(isopropoxylcarbonyl)ethyl]thiophosphorodiamidate;
4'-Fluoro-2'-methylcytidine-5'-{N,N'-bis[(S)-1-(isopropoxylcarbonyl)ethyl]phosphorodiamidate; and
4'-Fluoro-2'-methylcytidine-5'-{N,N'-bis[(S)-1-(isopropoxylcarbonyl)ethyl]thiophosphorodiamidate.

The application provides a method of treatment of HCV by administering to a patient in need thereof a combination of a compound of Formula I in and a compound of Formula II wherein the compound of Formula II is selected from the group consisting of:
2'-Deoxy-2',4'-difluoro-2'-methyluridine-5'-(O-phenyl-N-(S)-1-(isopropoxycarbonyl)ethyl thiophosphoramidate;
2'-Deoxy-2',4'-difluoro-2'-methyluridine-5'-(O-2-naphthyl-N-(S)-1-(isopropoxycarbonyl)ethyl thiosphosphoramidate;
2'-Deoxy-2',4'-difluoro-2'-methyluridine-5'-(O-1-naphthyl-N-(S)-1-(isopropoxycarbonyl)ethyl thiosphosphoramidate
2'-Deoxy-2',4'-difluoro-2'-methyluridine-3',5'-cyclic phosphoric acid isopropyl ester;
4'-Fluoro-2'-methyluridine-5'-(O-phenyl-N-(S)-1-(isopropoxycarbonyl)ethyl phosphoramidate;
4'-Fluoro-2'-methyluridine-5'-(O-1-naphthyl-N-(S)-1-(isopropoxycarbonyl)ethyl phosphoramidate;
4'-Fluoro-2'-methyluridine-5'-(O-1-naphthyl-N-(S)-2-(isopropoxycarbonyl)ethyl phosphoramidate;
4'-Fluoro-2'-methyluridine-5'-(O-phenyl-N-(S)-1-(isopropoxycarbonyl)ethyl thiophosphoramidate;
4'-Fluoro-2'-methyluridine-5'-(O-1-naphthyl-N-(S)-1-(isopropoxycarbonyl)ethyl thiophosphoramidate;
4'-Fluoro-2'-methyluridine-5'-(O-1-naphthyl-N-(S)-2-(isopropoxycarbonyl)ethyl thiophosphoramidate;
4'-Fluoro-2'-methyluridine-3',5'-cyclic phosphoric acid isopropyl ester;
4'-Fluoro-2'-methyluridine-3',5'-cyclic thiophosphoric acid isopropyl ester;
2'-Deoxy-2',4'-difluoro-2'-methyluridine-5'-{N,N'-bis[(S)-1-(isopropoxylcarbonyl)ethyl]phosphorodiamidate;
2'-Deoxy-2',4'-difluoro-2'-methyluridine-5'-{N,N'-bis[(S)-1-(isopropoxylcarbonyl)ethyl]thiophosphorodiamidate;
4'-Fluoro-2'-methyluridine-5'-{N,N'-bis[(S)-1-(isopropoxylcarbonyl)ethyl]phosphorodiamidate; and
4'-Fluoro-2'-methyluridine-5'-{N,N'-bis[(S)-1-(isopropoxylcarbonyl)ethyl]thiophosphorodiamidate.

The application provides a method of treatment of HCV by administering to a patient in need thereof a combination of a compound of Formula I in and a compound of Formula II wherein the compound of Formula II is selected from the group consisting of:
(S)-2-{[(2S,3S,4R,5R)-5-(2,4-Dioxo-3,4-dihydro-2H-pyrimidin-1-yl)-2,4-difluoro-3-hydroxy-4-methyl-tetrahydro-furan-2-ylmethoxy]-phenoxy-phosphorylamino}-propionic acid isopropyl ester;
(S)-2-[[(2S,3S,4R,5R)-5-(2,4-Dioxo-3,4-dihydro-2H-pyrimidin-1-yl)-2,4-difluoro-3-hydroxy-4-methyl-tetrahydro-furan-2-ylmethoxy]-(naphthalen-1-yloxy)-phosphorylamino]-propionic acid isopropyl ester;
(S)-2-[[(2S,3S,4R,5R)-5-(2,4-Dioxo-3,4-dihydro-2H-pyrimidin-1-yl)-2,4-difluoro-3-hydroxy-4-methyl-tetrahydro-furan-2-ylmethoxy]-(naphthalen-2-yloxy)-phosphorylamino]-propionic acid isopropyl ester;
(S)-2-[[(2S,3 S,4R,5R)-5-(2,4-dioxo-3,4-dihydro-2H-pyrimidin-1-yl)-2,4-difluoro-3-[((S)-1- isopropoxycarbonylethylamino)-(naphthalen-2-yloxy)-phosphoryloxy]-4-methyl-tetrahydro-furan-2-ylmethoxy]-(naphthalen-2-yloxy)-phosphorylamino]-propionicacid isopropyl ester;
(S)-2-[[(2S,3S,4R,5R)-5-(2,4-Dioxo-3,4-dihydro-2H-pyrimidin-1-yl)-2,4-difluoro-4-methyl-3-propionyloxy- tetrahydro-furan-2-ylmethoxy]-(naphthalen-1-yloxy)-phosphorylamino]-propionic acid isopropyl ester;
(S)-2-[(S)-[(2S,3S,4R,5R)-5-(2,4-Dioxo-3,4-dihydro-2H-pyrimidin-1-yl)-2,4-difluoro-3-hydroxy-4-methyl- tetrahydro-furan-2-ylmethoxy]-(naphthalen-2-yloxy)-phosphorylamino]-propionic acid isopropyl ester;
(S)-2-[(R)-[(2S,3S,4R,5R)-5-(2,4-Dioxo-3,4-dihydro-2H-pyrimidin-1-yl)-2,4-difluoro-3-hydroxy-4-methyl- tetrahydro-furan-2-ylmethoxy]-(naphthalen-2-yloxy)-phosphorylamino]-propionic acid isopropyl ester;
(S)-2-[(R)-[(2S,3S,4R,5R)-5-(2,4-Dioxo-3,4-dihydro-2H-pyrimidin-1-yl)-2,4-difluoro-3-hydroxy-4-methyl- tetrahydro-furan-2-ylmethoxy]-(naphthalen-1-yloxy)-phosphorylamino]-propionic acid isopropyl ester;
(S)-2-[(S)-[(2S,3S,4R,5R)-5-(2,4-Dioxo-3,4-dihydro-2H-pyrimidin-1-yl)-2,4-difluoro-3-hydroxy-4-methyl- tetrahydro-furan-2-ylmethoxy]-(naphthalen-1-yloxy)-phosphorylamino]-propionic acid isopropyl ester;
(S)-2-{(S)-[(2S,3 S,4R,5R)-5-(2,4-Dioxo-3,4-dihydro-2H-pyrimidin-1-yl)-2,4-difluoro-3-hydroxy-4-methyl- tetrahydro-furan-2-ylmethoxy]-phenoxy-phosphorylamino}-propionic acid isopropyl ester;
(S)-2-{(R)-[(2S,3 S,4R,5R)-5-(2,4-Dioxo-3,4-dihydro-2H-pyrimidin-1-yl)-2,4-difluoro-3-hydroxy-4-methyl- tetrahydro-furan-2-ylmethoxy]-phenoxy-phosphorylamino}-propionic acid isopropyl ester;
(S)-2-[(S)-[(2S,3 S,4R,5R)-5-(5-Bromo-2,4-dioxo-3,4-dihydro-2H-pyrimidin-1-yl)-2,4-difluoro-3-hydroxy-4-methyl-tetrahydro-furan-2-ylmethoxy]-(naphthalen-1-yloxy)-phosphorylamino]-propionic acid isopropyl ester;
(S)-2-[(S)-[(2S,3S,4R,5R)-5-(5-Bromo-2,4-dioxo-3,4-dihydro-2H-pyrimidin-1-yl)-2,4-difluoro-3-hydroxy-4-methyl-tetrahydro-furan-2-ylmethoxy]-(naphthalen-2-yloxy)-phosphorylamino]-propionic acid isopropyl ester;
(S)-2-[(R)-[(2S,3 S,4R,5R)-5-(5-Bromo-2,4-dioxo-3,4-dihydro-2H-pyrimidin-1-yl)-2,4-difluoro-3-hydroxy-4-methyl-tetrahydro-furan-2-ylmethoxy]-(naphthalen-1-yloxy)-phosphorylamino]-propionic acid isopropyl ester;
(S)-2-[(R)-[(2S,3 S,4R,5R)-5-(5-Bromo-2,4-dioxo-3,4-dihydro-2H-pyrimidin-1-yl)-2,4-difluoro-3-hydroxy-4-methyl-tetrahydro-furan-2-ylmethoxy]-(naphthalen-2-yloxy)-phosphorylamino]-propionic acid isopropyl ester; and
(S)-2-[[(2S,3 S,4R,5R)-5-(5-Bromo-2,4-dioxo-3,4-dihydro-2H-pyrimidin-1-yl)-2,4-difluoro-3-hydroxy-4- methyl-tetrahydro-furan-2-ylmethoxy]-(naphthalen-2-yloxy)-phosphorylamino]-propionic acid isopropyl ester.

The application provides a method of treatment of HCV by administering to a patient in need thereof a combination of a compound of Formula I in and a compound of Formula II further comprising one or more of ribavirin, peginterferon-α, simeprevir, ledipasvir, daclatasvir, and velpatasvir.

The application provides a method of treatment of HCV by administering to a patient in need thereof a composition comprising a compound of Formula I and a compound of Formula II, admixed with at least one carrier, diluent or excipient

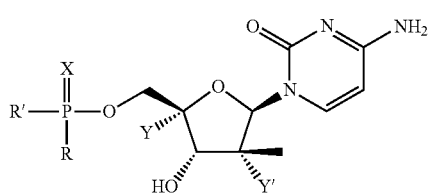

I

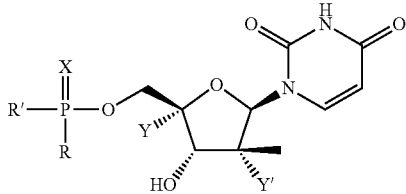

II wherein:
each R is independently O—R¹ or NHC(R²ᵃ)(R²ᵇ)C(=O)OR³;
each R' is independently O—R¹ or NHC(R²ᵃ)(R²ᵇ)C(=O)OR³;
each R¹ is independently phenyl or naphthyl, optionally substituted with one or more lower alkyl, lower alkoxy, halo, lower haloalkyl, or cyano;
each R²ᵃ and R²ᵇ are independently H or lower alkyl;
each R³ is independently H, lower alkyl, lower haloalkyl, phenyl or phenyl lower alkyl;
each X is independently O or S;
each Y is independently H or F; and
each Y' is independently F or OH;
or a pharmacologically acceptable salt thereof.

The application provides a method of treatment of HCV by administering to a patient in need thereof a compound of Formula I, or a combination of Formula I and Formula II, further in combination with a NS3A HCV protease inhibitor

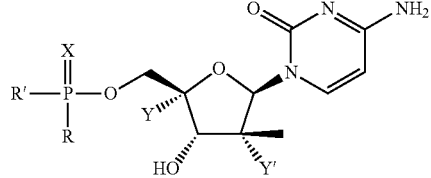

I

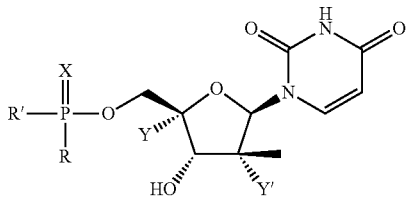

II wherein:
each R is independently O—R¹ or NHC(R²ᵃ)(R²ᵇ)C(=O)OR³;
each R' is independently O—R¹ or NHC(R²ᵃ)(R²ᵇ)C(=O)OR³;
each R¹ is independently phenyl or naphthyl, optionally substituted with one or more lower alkyl, lower alkoxy, halo, lower haloalkyl, or cyano;
each R²ᵃ and R²ᵇ are independently H or lower alkyl;
each R³ is independently H, lower alkyl, lower haloalkyl, phenyl or phenyl lower alkyl;
each X is independently O or S;
each Y is independently H or F; and
each Y' is independently F or OH;
or a pharmacologically acceptable salt thereof.

The application provides a method of treatment of HCV by administering to a patient in need thereof a compound of Formula I, or a combination of Formula I and Formula II, further in combination with an additional NS5B HCV polymerase inhibitor

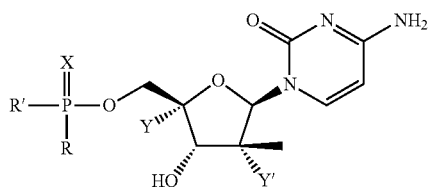

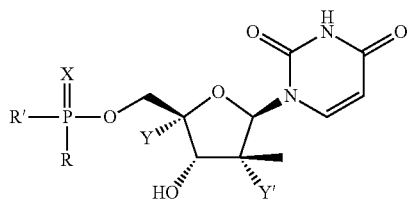

wherein:

each R is independently O—R¹ or NHC(R²ᵃ)(R²ᵇ)C(=O)OR³;

each R' is independently O—R¹ or NHC(R²ᵃ)(R²ᵇ)C(=)OR³;

each R¹ is independently phenyl or naphthyl, optionally substituted with one or more lower alkyl, lower alkoxy, halo, lower haloalkyl, or cyano;

each R¹ᵃ and R²ᵇ are independently H or lower alkyl;

each R³ is independently H, lower alkyl, lower haloalkyl, phenyl or phenyl lower alkyl;

each X is independently O or S;

each Y is independently H or F; and each Y' is independently F or OH;

or a pharmacologically acceptable salt thereof.

The application provides a use of a combination of the compound of Formula I and the compound of Formula II in the manufacture of a medicament for the treatment of HCV.

The application provides a compound, composition, or method as described herein.

Examples of representative compounds encompassed by the present invention and within the scope of the invention are provided in the following Tables. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on standard nucleic acid nomenclature common to one of ordinary skill in the art. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE 1

| Compound Number | Structure | Name |
|---|---|---|
| I-1 | 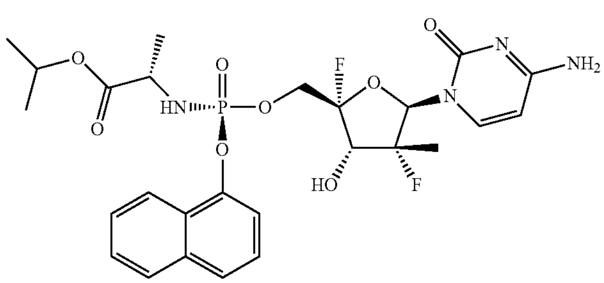 | isopropyl ((S)-((((2S,3S,4R,5R)-5-(4-amino-2-oxopyrimidin-1(2H)-yl)-2,4-difluoro-3-hydroxy-4-methyltetrahydrofuran-2-yl)methoxy)(naphthalen-1-yloxy)phosphoryl)-L-alaninate |
| I-2 | 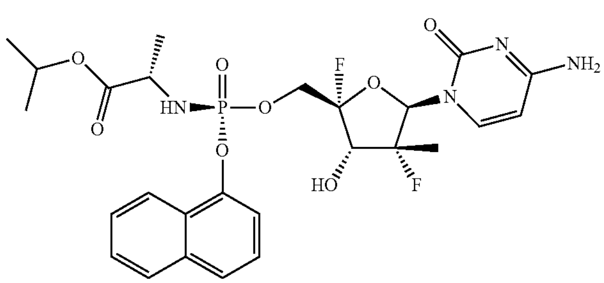 [SMILES: CC(C)OC(=O)[C@H](C)N[P@@](=O)(OC[C@@]1(F)O[C@@H](n2ccc(N)nc2=O)[C@](C)(F)[C@@H]1O)Oc1cccc2ccccc12] | isopropyl ((R)-((((2S,3S,4R,5R)-5-(4-amino-2-oxopyrimidin-1(2H)-yl)-2,4-difluoro-3-hydroxy-4-methyltetrahydrofuran-2-yl)methoxy)(naphthalen-1-yloxy)phosphoryl)-L-alaninate |

TABLE 1-continued

| Compound Number | Structure | Name |
|---|---|---|
| I-3 | 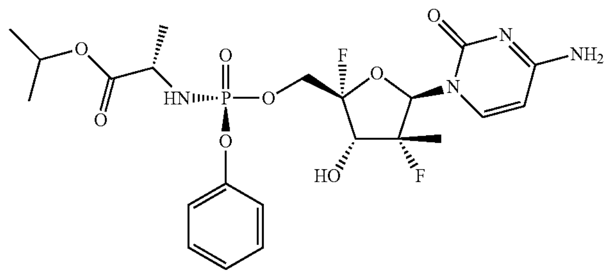 [SMILES: CC(C)OC(=O)[C@H](C)N[P@](=O)(OC[C@@]1(F)O[C@@H](n2ccc(N)nc2=O)[C@](C)(F)[C@@H]1O)Oc1ccccc1] | isopropyl ((S)-(((2S,3S,4R,5R)-5-(4-amino-2-oxopyrimidin-1(2H)-yl)-2,4-difluoro-3-hydroxy-4-methyltetrahydrofuran-2-yl)methoxy)(phenoxy)phosphoryl)-L-alaninate |
| I-4 | 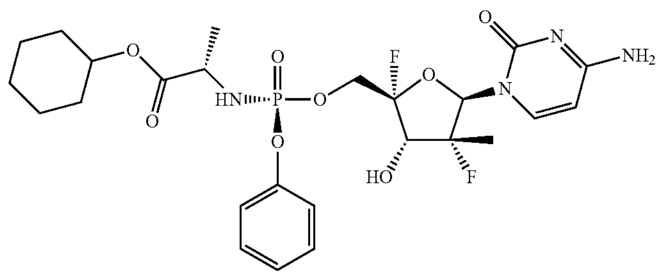 [SMILES: C[C@H](N[P@](=O)(OC[C@@]1(F)O[C@@H](n2ccc(N)nc2=O)[C@](C)(F)[C@@H]1O)Oc1ccccc1)C(=O)OC1CCCCC1] | cyclohexyl ((S)-(((2S,3S,4R,5R)-5-(4-amino-2-oxopyrimidin-1(2H)-yl)-2,4-difluoro-3-hydroxy-4-methyltetrahydrofuran-2-yl)methoxy)(phenoxy)phosphoryl)-L-alaninate |
| I-5 | 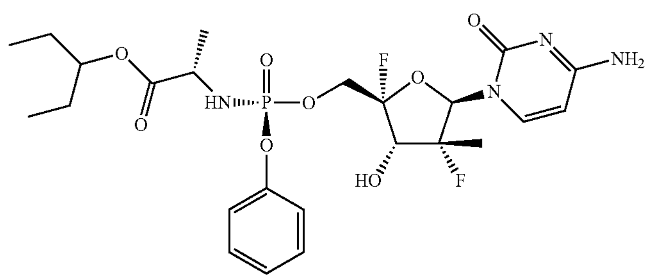 [SMILES: CCC(CC)OC(=O)[C@H](C)N[P@](=O)(OC[C@@]1(F)O[C@@H](n2ccc(N)nc2=O)[C@](C)(F)[C@@H]1O)Oc1ccccc1] | pentan-3-yl ((S)-(((2S,3S,4R,5R)-5-(4-amino-2-oxopyrimidin-1(2H)-yl)-2,4-difluoro-3-hydroxy-4-methyltetrahydrofuran-2-yl)methoxy)(phenoxy)phosphoryl)-L-alaninate |
| I-6 | 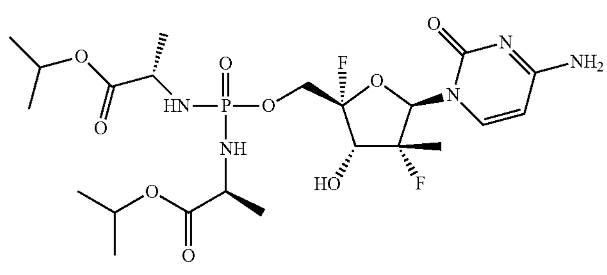 [SMILES: CC(C)OC(=O)[C@H](C)NP(=O)(N[C@@H](C)C(=O)OC(C)C)OC[C@@]1(F)O[C@@H](n2ccc(N)nc2=O)[C@](C)(F)[C@@H]1O] | Diisopropyl ((((2S,3S,4R,5R)-5-(4-amino-2-oxopyrimidin-1(2H)-yl)-2,4-difluoro-3-hydroxy-4-methyltetrahydrofuran-2-yl)methoxy)((amino)phosphoryl)-L-alaninate |
| I-7 | 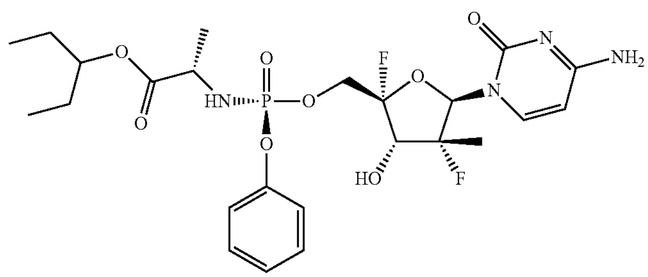 [SMILES: CCC(CC)OC(=O)[C@H](C)N[P@](=O)(OC[C@@]1(F)O[C@@H](n2ccc(N)nc2=O)[C@](C)(F)[C@@H]1O)Oc1ccccc1] | Dicyclohexyl ((((2S,3S,4R,5R)-5-(4-amino-2-oxopyrimidin-1(2H)-yl)-2,4-difluoro-3-hydroxy-4-methyltetrahydrofuran-2-yl)methoxy)((amino)phosphoryl)-L-alaninate |

TABLE 1-continued

| Compound Number | Structure | Name |
|---|---|---|
| I-8 | 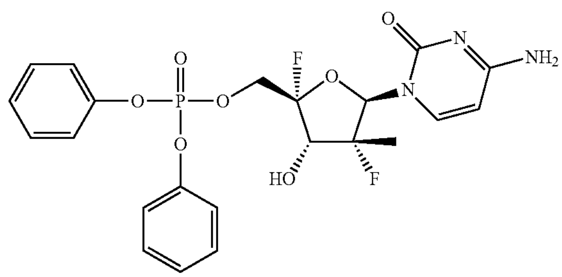 [SMILES: C[C@]1(F)[C@H](n2ccc(N)nc2=O)O[C@](F)(COP(=O)(Oc2ccccc2)Oc2ccccc2)[C@H]1O] | ((2S,3S,4R,5R)-5-(4-amino-2-oxopyrimidin-1(2H)-yl)-2,4-difluoro-3-hydroxy-4-methyltetrahydrofuran-2-yl)methyl diphenyl phosphate |
| I-9 | 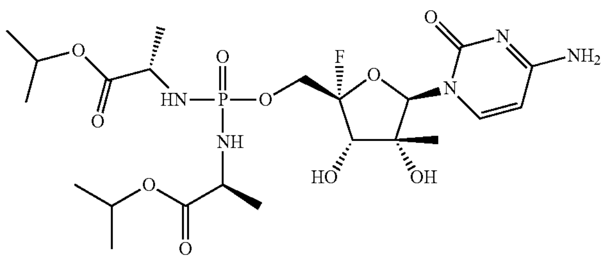 [SMILES: CC(C)OC(=O)[C@H](C)NP(=O)(N[C@@H](C)C(=O)OC(C)C)OC[C@@]1(F)O[C@@H](n2ccc(N)nc2=O)[C@](C)(O)[C@@H]1O] | Diisopropyl ((((2S,3S,4R,5R)-5-(4-amino-2-oxopyrimidin-1(2H)-yl)-2-fluoro-3,4-dihydroxy-4-methyltetrahydrofuran-2-yl)methoxy)((amino)phosphoryl)-L-alaninate |
| I-10 | 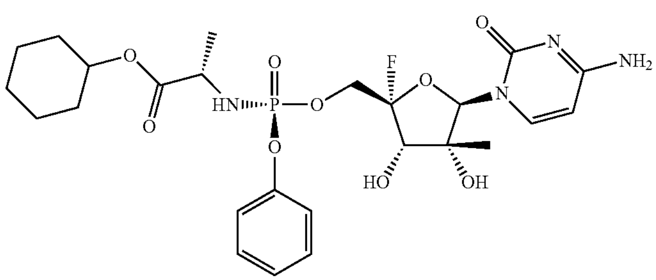 [SMILES: C[C@H](N[P@](=O)(OC[C@@]1(F)O[C@@H](n2ccc(N)nc2=O)[C@](C)(O)[C@@H]1O)Oc1ccccc1)C(=O)OC1CCCCC1] | cyclohexyl ((S)-(((2S,3S,4R,5R)-5-(4-amino-2-oxopyrimidin-1(2H)-yl)-2-fluoro-3,4-dihydroxy-4-methyltetrahydrofuran-2-yl)methoxy)(phenoxy)phosphoryl)-L-alaninate |
| I-11 | 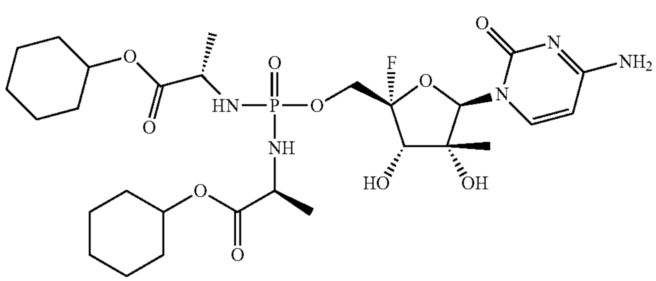 [SMILES: C[C@H](NP(=O)(N[C@@H](C)C(=O)OC1CCCCC1)OC[C@@]1(F)O[C@@H](n2ccc(N)nc2=O)[C@](C)(O)[C@@H]1O)C(=O)OC1CCCCC1] | Dicyclohexyl ((((2S,3S,4R,5R)-5-(4-amino-2-oxopyrimidin-1(2H)-yl)-2-fluoro-3,4-dihydroxy-4-methyltetrahydrofuran-2-yl)methoxy)((amino)phosphoryl)-L-alaninate |
| I-12 | 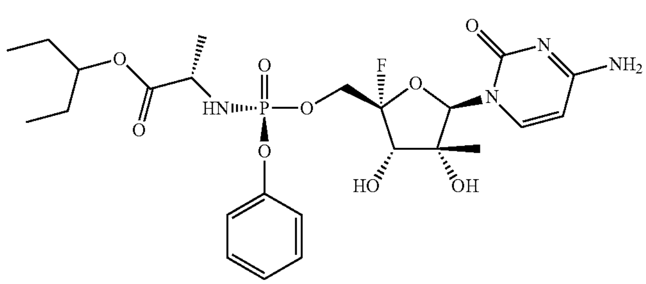 [SMILES: CCC(CC)OC(=O)[C@H](C)N[P@](=O)(OC[C@@]1(F)O[C@@H](n2ccc(N)nc2=O)[C@](C)(O)[C@@H]1O)Oc1ccccc1] | pentan-3-yl ((S)-(((2S,3S4R,5R)-5-(4-amino-2-oxopyrimidin-1(2H)-yl)-2-fluoro-3,4-dihydroxy-4-methyltetrahydrofuran-2-yl)methoxy)(phenoxy)phosphoryl)-L-alaninate |

TABLE 1-continued

| Compound Number | Structure | Name |
|---|---|---|
| I-13 | 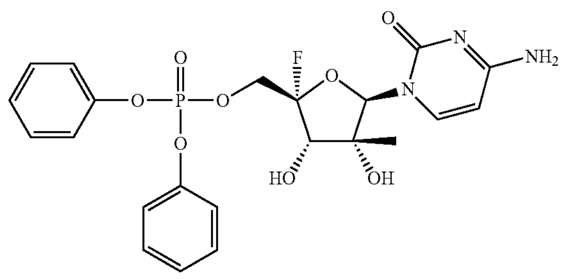 [SMILES: C[C@]1(O)[C@H](n2ccc(N)nc2=O)O[C@](F)(COP(=O)(Oc2ccccc2)Oc2ccccc2)[C@H]1O] | ((2S,3S,4R,5R)-5-(4-amino-2-oxopyrimidin-1(2H)-yl)-2-fluoro-3,4-dihydroxy-4-methyltetrahydrofuran-2-yl)methyl diphenyl phosphate |
| I-14 | 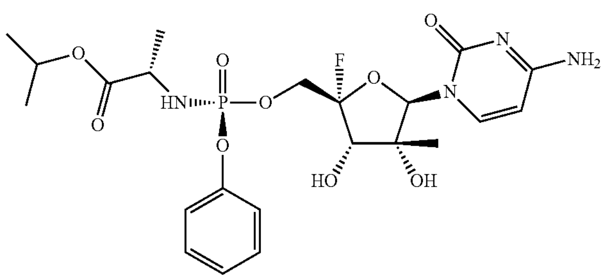 [SMILES: CC(C)OC(=O)[C@H](C)N[P@](=O)(OC[C@@]1(F)O[C@@H](n2ccc(N)nc2=O)[C@](C)(O)[C@@H]1O)Oc1ccccc1] | isopropyl ((S)-(((2S,3S,4R,5R)-5-(4-amino-2-oxopyrimidin-1(2H)-yl)-2-fluoro-3,4-dihydroxy-4-methyltetrahydrofuran-2-yl)methoxy)(phenyoxy)phosphoryl)-L-alaninate |
| I-15 | 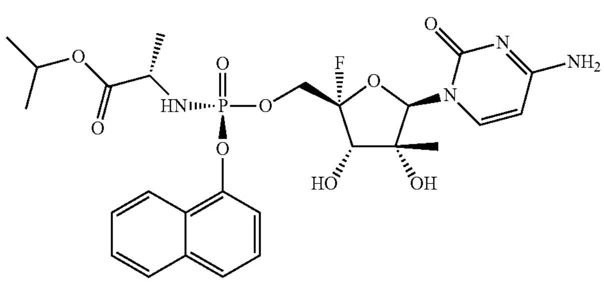 | isopropyl ((S)-(((2S,3S,4R,5R)-5-(4-amino-2-oxopyrimidin-1(2H)-yl)-2-fluoro-3,4-dihydroxy-4-methyltetrahydrofuran-2-yl)methoxy)(naphthalen-1-yloxy)phosphoryl)-L-alaninate |

EXAMPLES

Abbreviations used in this application include: acetyl (Ac), acetic acid (HOAc), azo-bis-isobutyrylnitrile (AIBN), 1-N-hydroxybenzotriazole (HOBt), atmospheres (Atm), high pressure liquid chromatography (HPLC), 9-borabicyclo[3.3.1]nonane (9-BBN or BBN), methyl (Me), tert-butoxycarbonyl (Boc), acetonitrile (MeCN), di-tert-butyl pyrocarbonate or boc anhydride ($BOC_2O$), 1-(3-dimethylaminopropyl)-3-ethylcarbodiimide hydrochloride (EDCI), benzoyl (Bz), benzyl (Bn), m-chloroperbenzoic acid (MCPBA), butyl (Bu), methanol (MeOH), benzyloxycarbonyl (cbz or Z), melting point (mp), carbonyl diimidazole (CDI), $MeSO_2$— (mesyl or Ms), 1,4-diazabicyclo[2.2.2]octane (DABCO), mass spectrum (ms) diethylaminosulfur trifluoride (DAST), methyl t-butyl ether (MTBE), dibenzylideneacetone (Dba), N-carboxyanhydride (NCA), 1,5-diazabicyclo[4.3.0]non-5-ene (DBN), N-bromosuccinimide (NBS), 1,8-diazabicyclo[5.4.0]undec-7-ene (DBU), N-methylmorpholine (NMM), N-methylpyrrolidone (NMP), 1,2-dichloroethane (DCE), pyridinium chlorochromate (PCC), N,N'-dicyclohexylcarbodiimide (DCC), pyridinium dichromate (PDC), dichloromethane (DCM), propyl (Pr), diethyl azodicarboxylate (DEAD), phenyl (Ph), di-iso-propylazodicarboxylate, DIAD, pounds per square inch (psi), di-iso-propylethylamine (DIPEA), pyridine (pyr), di-iso-butylaluminumhydride, DIBAL-H, room temperature, rt or RT, N,N-dimethyl acetamide (DMA), tert-butyldimethylsilyl or t-$BuMe_2Si$, (TBDMS), 4-N,N-dimethylaminopyridine (DMAP), triethylamine ($Et_3N$ or TEA), N,N-dimethylformamide (DMF), triflate or $CF_3SO_2$-(Tf), dimethyl sulfoxide (DMSO), trifluoroacetic acid (TFA), 1,1'-bis-(diphenylphosphino)ethane (dppe), 2,2,6,6-tetramethylheptane-2,6-dione (TMHD), 1,1'-bis-(diphenylphosphino)ferrocene (dppf), thin layer chromatography (TLC), ethyl acetate (EtOAc), tetrahydrofuran (THF), diethyl ether ($Et_2O$), trimethylsilyl or $Me_3Si$ (TMS), ethyl (Et), p-toluenesulfonic acid monohydrate (TsOH or pTsOH), lithium hexamethyl disilazane (LiHMDS), 4-Me-$C_6H_4SO_2$— or tosyl (Ts), iso-propyl N-urethane-N-carboxyanhydride (UNCA), ethanol (EtOH). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

General Conditions

Compounds of the invention can be made by a variety of methods depicted in the illustrative synthetic reactions described below in the Examples section.

The starting materials and reagents used in preparing these compounds generally are either available from commercial suppliers, such as Aldrich Chemical Co., or are prepared by methods known to those skilled in the art following procedures set forth in references such as Fieser and Fieser's *Reagents for Organic Synthesis*; Wiley & Sons: New York, 1991, Volumes 1-15; Rodd's *Chemistry of Carbon Compounds*, Elsevier Science Publishers, 1989, Volumes 1-5 and Supplementals; and *Organic Reactions*, Wiley & Sons: New York, 1991, Volumes 1-40. It should be appreciated that the synthetic reaction schemes shown in the Examples section are merely illustrative of some methods by which the compounds of the invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein are typically conducted under an inert atmosphere at atmospheric pressure at a reaction temperature range of from about −78° C. to about 150° C., often from about 0° C. to about 125° C., and more often and conveniently at about room (or ambient) temperature, e.g., about 20° C.

Various substituents on the compounds of the invention can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups are known in the art, and can be employed. Examples of many of the possible groups can be found in "*Protective Groups in Organic Synthesis*" by Green et al., John Wiley and Sons, 1999. For example, nitro groups can be added by nitration and the nitro group can be converted to other groups, such as amino by reduction, and halogen by diazotization of the amino group and replacement of the diazo group with halogen. Acyl groups can be added by Friedel-Crafts acylation. The acyl groups can then be transformed to the corresponding alkyl groups by various methods, including the Wolff-Kishner reduction and Clemmenson reduction. Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product, including isolated products.

The starting material 1 can be prepared according to the procedures described by Sofia, M. J. et al, *J. Med. Chem.* (2010), 53(19),7202-7218 and Clark, J. L. et al, *J. Med. Chem.* (2005), 48(17),5504-5508. Iodination followed by elimination of iodide under basic condition can lead to intermediate 2, in which protection of 3'-hydroxy with benzoyl group, followed by a key stereospecific fluorination reaction to give intermediate 4. Similar transformation to install a fluoride at 4' α position has been described previously by Ajmera, S. et al, *J. Med. Chem.* (1988), 31(6),1094-1098 and Moffatt, J. G. et al, *J. Am. Chem. Soc.* (1971), 93(17), 4323-4324. Displacement of 5' iodide with sodium benzoate followed by deprotection of 3', 5' benzoyl groups gives the nucleoside intermediate 4 (Scheme 1).

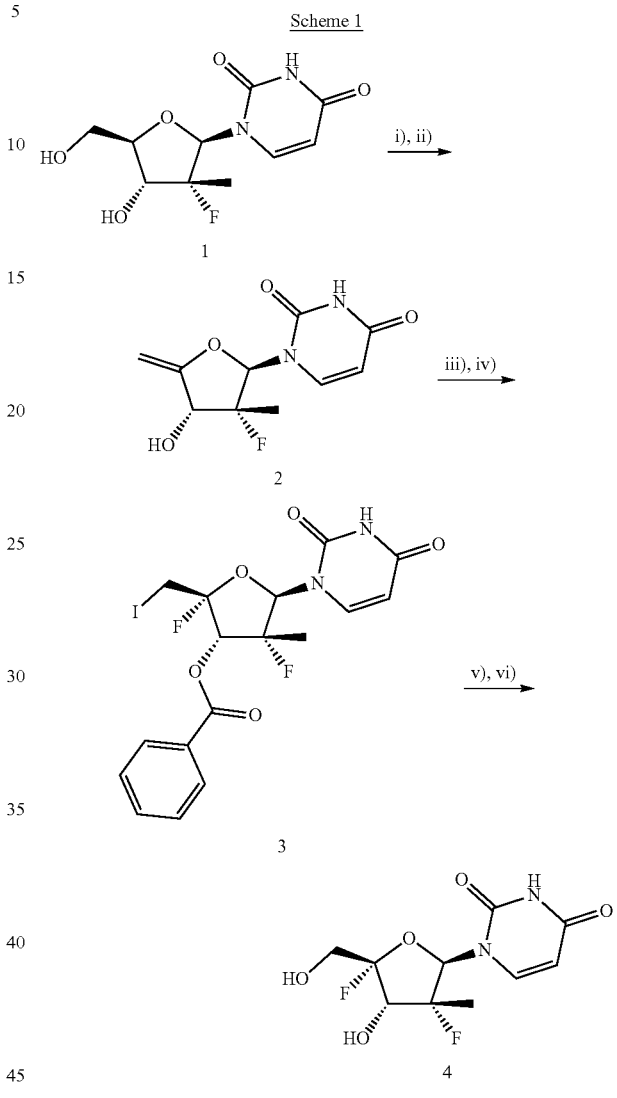

i) I$_2$, PPh$_3$, THF; ii) NaOMe, MeOH; iii) BzCl, DMAP, THF; iv) I$_2$, AgF, CH$_2$Cl$_2$; v) PhCO$_2$Na, DMSO; vi) NH$_3$, MeOH Compound 12 can be prepared by those skilled in the art of organic synthesis following the synthetic sequence outlined below. Thus, protection, iodination and then elimination under basic conditions should yield the intermediate 7. Fluorination at the 4'-position has previously been reported by Ajmera, S. et al, *J. Med. Chem.* (1988), 31(6), 1094-1098 and Moffatt, J. G. et al, *J. Am. Chem. Soc.* (1971), 93(17), 4323-4324. Displacement of 5' iodide 8 with sodium benzoate should afford intermediate 9. Deprotection followed by selective protection of the 3' and 5'-hydroxy group with 1,3-dichloro-1,1,3,3-tetraisopropyldisiloxane (DIPSC1) and then oxidation under Dess-Martin conditions is expected to yield the ketone 11, following a similar method described by Hayakawa, H et al., *Chem. Pharm. Bull.*, (1987), 35(6), 2605-2608. Deprotection under standard conditions to remove a silyl protecting group should yield the desired product 12 (Scheme 2).

Scheme 2

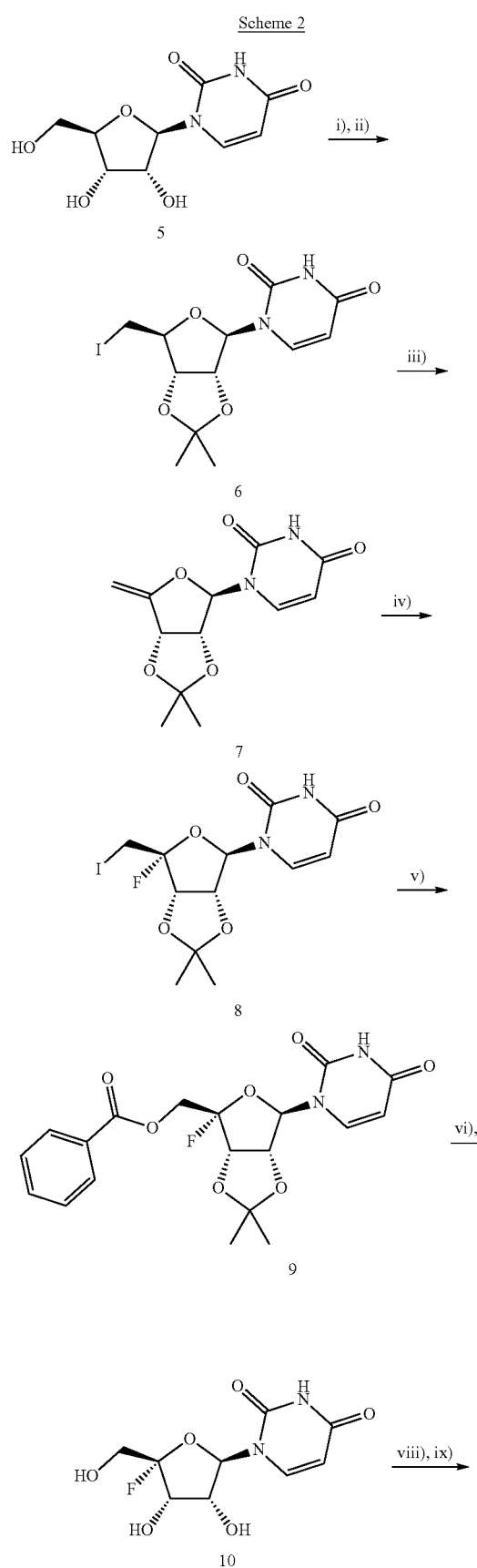

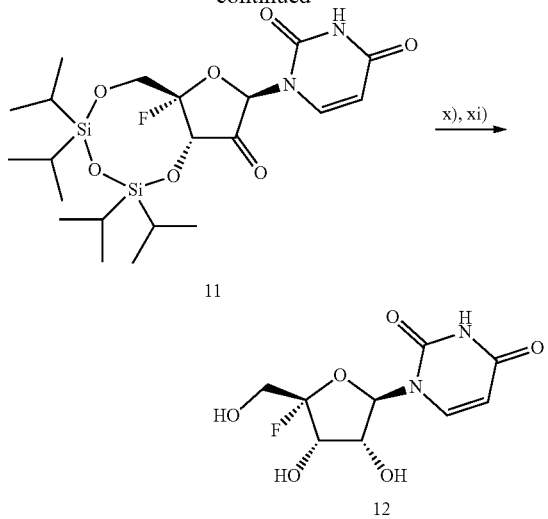

i) Acetone, PTSA; ii) $I_2$, $PPh_3$, THF; iii) NaOMe, MeOH; iv) $I_2$, AgF, $CH_2Cl_2$; v) $PhCO_2Na$, DMSO; vi) $NH_3$, MeOH; vii) Formic acid; viii) DIPSCl, Pyridine; ix) Dess-Martin, $CH_2Cl_2$; x) $AlCl_3$, $CH_2Cl_2$; xi) TBAF, THF.

Phosphoramidate compounds of the present invention can be prepared by condensation of nucleoside 4 or 12 with a suitably substituted phosphochloridate, or its sulfur analogue, of type 13 in the presence of a strong base (Scheme 3). The coupled product 16 of Formula I is obtained as a mixture of two diastereomers initially under the coupling reaction and can be separated into their corresponding chiral enantiomers by chiral column, chiral HPLC, or chiral SFC chromatography.

Scheme 3

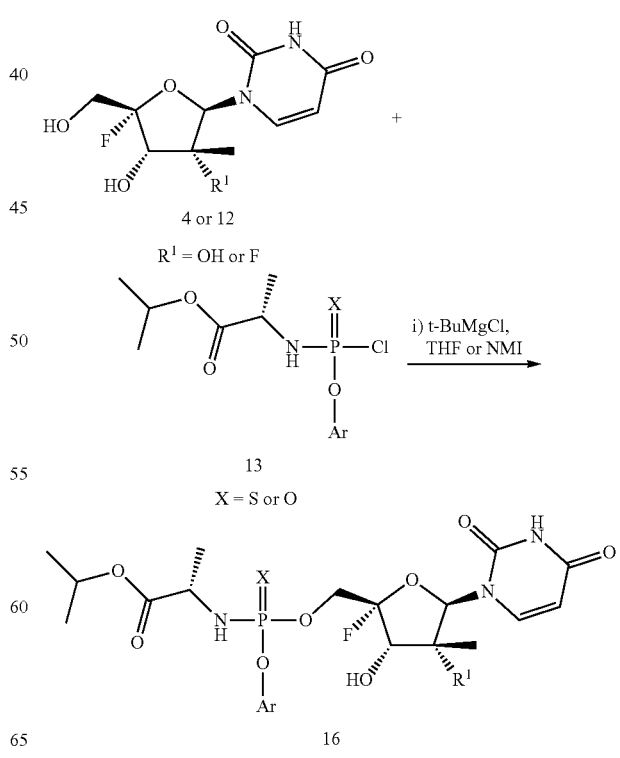

Phosphorodiamidate compounds of Formula I in the present invention can be prepared by condensation of nucleoside 4 or 12 with a suitably substituted phosphorodiamidic chloride, or phosphorodiamidothioic chloride, of type 17 in the presence of a strong base (Scheme 4).

Scheme 4

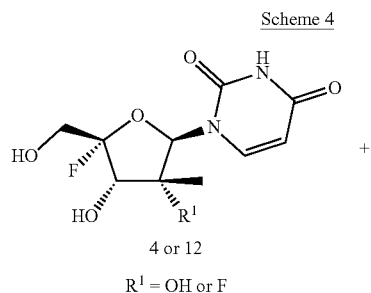

4 or 12

R¹ = OH or F

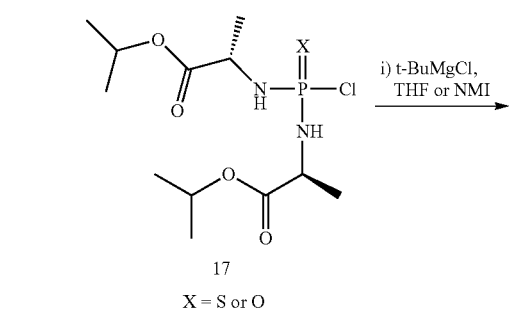

17

X = S or O

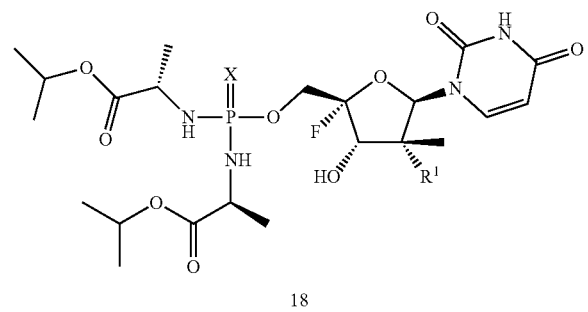

18

Phosphates of the present invention can be prepared by condensation of nucleoside 4 or 12 with isopropyl N,N,N,N-tetraisopropylphosphorodiamidite 19 (Scheme 5). Conversion to the thio derivative can be performed by heating the crude reaction mixture with bis(3-triethoxylsilyl)propyl-tetrasulfide (TEST).

Scheme 5

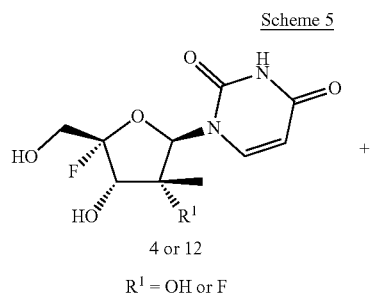

4 or 12

R¹ = OH or F

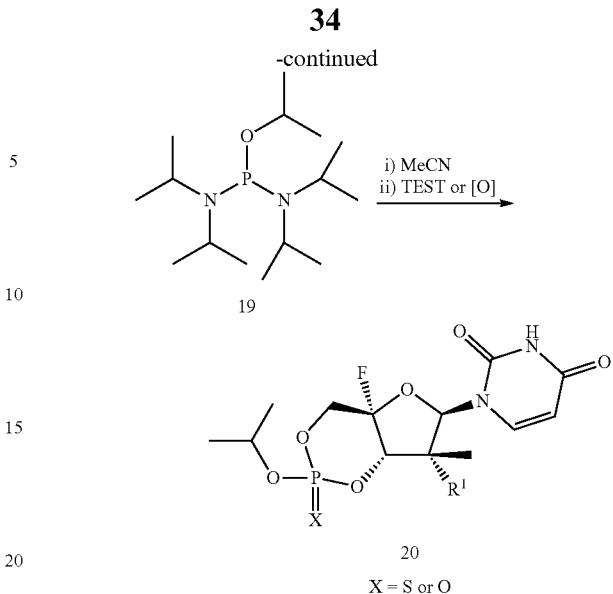

19

20

X = S or O

Biological Examples

HCV Replicon Assay

This assay measures the ability of the compounds of Formula I to inhibit HCV RNA replication, and therefore their potential utility for the treatment of HCV infections. The assay utilizes a reporter as a simple readout for intracellular HCV replicon RNA level. The *Renilla luciferase* gene is introduced into the first open reading frame of a genotype 1b replicon construct NK5.1 (N. Krieger et al., *J. Virol.* 2001 75(10):4614), immediately after the internal ribosome entry site (IRES) sequence, and fused with the neomycin phosphotransferase (NPTII) gene via a self-cleavage peptide 2A from foot and mouth disease virus (M. D. Ryan & J. Drew, *EMBO* 1994 13(4):928-933). After in vitro transcription the RNA is electroporated into human hepatoma Huh7 cells, and G418-resistant colonies are isolated and expanded. Stably selected cell line 2209-23 contains replicative HCV subgenomic RNA, and the activity of *Renilla luciferase* expressed by the replicon reflects its RNA level in the cells. The assay is carried out in duplicate plates, one in opaque white and one in transparent, in order to measure the anti-viral activity and cytotoxicity of a chemical compound in parallel ensuring the observed activity is not due to decreased cell proliferation or due to cell death.

HCV replicon cells (2209-23), which express *Renilla luciferase* reporter, are cultured in Dulbecco's MEM (Invitrogen cat no. 10569-010) with 5% fetal bovine serum (FBS, Invitrogen cat. no. 10082-147) and plated onto a 96-well plate at 5000 cells per well, and incubated overnight. Twenty-four hours later, different dilutions of chemical compounds in the growth medium are added to the cells, which are then further incubated at 37° C. for three days. At the end of the incubation time, the cells in white plates are harvested and luciferase activity is measured by using the *R. luciferase* Assay system (Promega cat no. E2820). All the reagents described in the following paragraph are included in the manufacturer's kit, and the manufacturer's instructions are followed for preparations of the reagents. The cells are washed once with 100 μL of phosphate buffered saline (pH 7.0) (PBS) per well and lysed with 20 μl of 1× *R. luciferase* Assay lysis buffer prior to incubation at room temperature for 20 min. The plate is then inserted into the Centro LB 960 microplate luminometer (Berthold Technologies), and 100 μl of *R. luciferase* Assay buffer is injected into each well and the signal measured using a 2-second delay, 2-second measurement program. $IC_{50}$, the concentration of the drug required for reducing replicon level by 50% in relation to the untreated cell control value, can be calculated from the plot of percentage reduction of the luciferase activity vs. drug concentration as described above.

WST-1 reagent from Roche Diagnostic (cat no. 1644807) is used for the cytotoxicity assay. Ten microliter of WST-1 reagent is added to each well of the transparent plates including wells that contain media alone as blanks. Cells are then incubated for 2 h at 37° C., and the OD value is measured using the MRX Revelation microtiter plate reader (Lab System) at 450 nm (reference filter at 650 nm). Again $CC_{50}$, the concentration of the drug required for reducing cell proliferation by 50% in relation to the untreated cell control value, can be calculated from the plot of percentage reduction of the WST-1 value vs. drug concentration as described above.

Combination Therapy Assays Protocols and Results

Methods

1. Cell Culture Medium

DMEM Growth Medium contains Dulbecco's Modification of Eagle's Medium (DMEM) supplemented with 10% heat-inactivated fetal bovine serum (FBS), 1×MEM non-essential amino acids, 2 mM L-glutamine, 100 IU/ml penicillin and 100 μg/ml streptomycin.

HCV Replicon Assay Medium contains DMEM-Phenol Red Free supplemented with 5% heat-inactivated FBS, 1× MEM non-essential amino acids, 2 mM L-glutamine, 100 IU/ml penicillin and 100 μg/ml streptomycin.

2. Cell Culture

HCV 1b replicon cells, which express a bicistronic genotype 1b replicon in Huh7-Lunet cells, were cultured at 37° C. with 5% $CO_2$ in DMEM Growth Medium plus 250 μg/ml G418.

3. Antiviral Combination Assays

HCV inhibitor combination assays were performed in HCV 1b replicon cells. HCV 1b replicon cells were seeded at the density of 4000 cells/well/100 μl in 96-well flat-bottom white plates 24 hrs prior to the compound treatment. For the drug combination studies, compound stock solutions (1.75 mM RBS1154 and 1 mM RBS1501 in 100% DMSO) were diluted 100-fold in replicon assay medium, yielding 17.5 μM RBS1154 and 10 μM RBS1501 in 1% DMSO, respectively. Both compounds were then serially diluted 1.5-fold in replicon assay medium with 1% DMSO to obtain 10-time concentrated range of concentrations ~1.75-0.068 μM for RBS1154 and 1-0.088 μM for RBS1501, respectively. 12.5 μl of these 10-time concentrated serial dilution of RBS1154 (Horizontal drug) and 12.5 μl of RBS1501 (Vertical drug) were added to the replicon cells. The final concentration of DMSO in the cell culture medium for all testing points were 0.2%. Three days after the treatment, the antiviral activities were determined by measuring replicon luciferase activity by adding 70 μl/well of One-Glo® reagent (Promega). The relative light units (RLU) were measured using a Perkin Elmer EnSpire reader set to read for 0.5 sec/well. The drug treatment scheme for RBS1154 and RBS1501 in combination were generated using the template shown in Table 1.

4. Data Analysis

Data were analyzed using the MacSynergy™ II program developed by Prichard and Shipman. The combination effect of each pair of inhibitors was calculated by the volume of surface deviations (volumes are expressed as μM concentration times μM concentration times percentage, or $\mu M^2 \%$) at 95% confidence, Bonferroni Adjusted.

TABLE 1

Compound Treatment Template for Combination Studies

| Vertical drug | | Horizontal drug RBS1154 Concentration ranges [M] | | | | | | | | | | | |
|---|---|---|---|---|---|---|---|---|---|---|---|---|---|
| I-1 | | 0 | 0.068 | 0.102 | 0.154 | 0.230 | 0.346 | 0.519 | 0.778 | 1.167 | 1.75 | | |
| Concentration ranges [μM] | 1 | X | X | X | X | X | X | X | X | X | X | VC | CC |
| | 0.667 | X | X | X | X | X | X | X | X | X | X | VC | CC |
| | 0.444 | X | X | X | X | X | X | X | X | X | X | VC | CC |
| | 0.296 | X | X | X | X | X | X | X | X | X | X | VC | CC |
| | 0.198 | X | X | X | X | X | X | X | X | X | X | VC | CC |
| | 0.132 | X | X | X | X | X | X | X | X | X | X | VC | CC |
| | 0.088 | X | X | X | X | X | X | X | X | X | X | VC | CC |
| | 0 | X | X | X | X | X | X | X | X | X | X | VC | CC |

VC: vehicle control (0.2% DMSO)
CC: cell control (no cells, replicon assay medium only)

Results

| Drug 1 | Drug 2 | Synergy | Antagonism | | Nuc Combo | Max % I | Min % I | Max % SD | Min % SD |
|---|---|---|---|---|---|---|---|---|---|
| Sofosbuvir | Sofosbuvir | 11 | −6.5 | additive | U:U | 100 | 42.85 | 4.57 | 0 |
| II-1 | Sofosbuvir | 8.7 | −9.2 | additive | U:U | 100 | 31.56 | 6.23 | 0 |
| II-1 | Sofosbuvir | 59 | −11 | mod syn | U:U | 99.9 | 24.62 | 9.66 | 0 |
| II-1 | I-1 | 115 | −10 | strong syn | U:C | 99.8 | 5.43 | 6.14 | 0 |
| II-1 | I-1 | 66 | −12 | mod syn | U:C | 99.7 | 3.78 | 13.37 | 0.01 |
| Sofosbuvir | I-1 | 59 | −15 | mod syn | U:C | 99.9 | 9.2 | 11.08 | 0.01 |
| Sofosbuvir | I-1 | 815 | −1.6 | strong syn | U:C | 99.5 | −2.12 | 9.49 | 0 |
| Sofosbuvir | I-1 | 238 | −32 | strong syn | U:C | 99.8 | −4.15 | 11.93 | 0.03 |
| II-1 | I-1 | 309 | −5.2 | strong syn | U:C | 99.3 | −9.15 | 15.72 | 0.01 |
| II-1 | I-1 | 143 | −25 | strong syn | U:C | 99.7 | 10.79 | 8.02 | 0 |
| II-1 | I-3 | 148 | −8.3 | strong syn | U:C | 99.5 | −2.07 | 12.35 | 0.03 |

Dosage and Administration

As shown in above Table the compounds of Formula I have the potential to be efficacious as antiviral drugs for the treatment of HCV infections in humans, or are metabolized to a compound that exhibit such activity.

In another embodiment of the invention, the active compound or its prodrug derivative or salt can be administered in combination with another antiviral agent, such as an anti-hepatitis agent, including those of Formula I. When the active compound or its derivative or salt are administered in combination with another antiviral agent the activity may be increased over the parent compound. This can easily be assessed by preparing the derivative and testing its anti-HCV activity according to the method described herein.

Administration of the active compound may range from continuous (intravenous drip) to several oral administrations per day (for example, Q.I.D) and may include oral, topical parenteral, intramuscular, intravenous, subcutaneous, transdermal (which may include a penetration enhancement agent), buccal and suppository administration, among other routes of administration.

The 4'-F substituted nucleoside derivatives as well as their pharmaceutically useable salts, can be used as medicaments in the form of any pharmaceutical formulation. The pharmaceutical formulation can be administered enterally, either orally, e.g. in the form of tablets, coated tablets, dragées, hard and soft gelatin capsules, solutions, emulsions, syrups, or suspensions, or rectally, e.g. in the form of suppositories. They can also be administered parenterally (intramuscularly, intravenously, subcutaneously or intrasternal injection or infusion techniques), e.g. in the form of injection solutions, nasally, e.g. in the form of nasal sprays, or inhalation spray, topically and so forth.

For the manufacture of pharmaceutical preparations, the 4'-substituted nucleoside derivatives, as well as their pharmaceutically useable salts, can be formulated with a therapeutically inert, inorganic or organic excipient for the production of tablets, coated tablets, dragées, hard and soft gelatin capsules, solutions, emulsions or suspensions.

The compounds of Formula I can be formulated in admixture with a pharmaceutically acceptable carrier. For example, the compounds of the present invention can be administered orally as pharmacologically acceptable salts. Because the compounds of the present invention are mostly water soluble, they can be administered intravenously in physiological saline solution (e.g., buffered to a pH of about 7.2 to 7.5). Conventional buffers such as phosphates, bicarbonates or citrates can be used for this purpose. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) which are well within the ordinary skill in the art. It is also well within the ordinary skill of the art to modify the route of administration and dosage regimen of a particular compound in order to manage the pharmacokinetics of the present compounds for maximum beneficial effect in patients.

For parenteral formulations, the carrier will usually comprise sterile water or aqueous sodium chloride solution, though other ingredients including those which aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

Suitable excipients for tablets, coated tablets, dragées, and hard gelatin capsules are, for example, lactose, corn starch and derivatives thereof, talc, and stearic acid or its salts.

If desired, the tablets or capsules may be enteric-coated or sustained release by standard techniques.

Suitable excipients for soft gelatin capsules are, for example, vegetable oils, waxes, fats, semi-solid and liquid polyols.

Suitable excipients for injection solutions are, for example, water, saline, alcohols, polyols, glycerin or vegetable oils.

Suitable excipients for suppositories are, for example, natural and hardened oils, waxes, fats, semi-liquid or liquid polyols.

Suitable excipients for solutions and syrups for enteral use are, for example, water, polyols, saccharose, invert sugar and glucose.

The pharmaceutical preparations of the present invention may also be provided as sustained release formulations or other appropriate formulations.

The pharmaceutical preparations can also contain preservatives, solubilizers, stabilizers, wetting agents, emulsifiers, sweeteners, colorants, flavourants, salts for adjustment of the osmotic pressure, buffers, masking agents or antioxidants.

The pharmaceutical preparations may also contain other therapeutically active agents known in the art.

The dosage can vary within wide limits and will, of course, be adjusted to the individual requirements in each particular case. For oral administration, a daily dosage of between about 0.01 and about 100 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 100 mg/kg body weight per day. A typical preparation will contain from about 5% to about 95% active compound (w/w). The daily dosage can be administered as a single dosage or in divided dosages, typically between 1 and 5 dosages per day.

In certain pharmaceutical dosage forms, the pro-drug form of the compounds, especially including acylated (acetylated or other) derivatives, pyridine esters and various salt forms of the present compounds are preferred. One of ordinary skill in the art will recognize how to readily modify the present compounds to pro-drug forms to facilitate delivery of active compounds to a target site within the host organism or patient. One of ordinary skill in the art will also take advantage of favorable pharmacokinetic parameters of the pro-drug forms, where applicable, in delivering the present compounds to targeted site within the host organism or patient to maximize the intended effect of the compound.

Indications and Method of Treatment

The compounds of the invention and their isomeric forms and pharmaceutically acceptable salts thereof are useful in treating and preventing HCV infection.

The application provides a method for treating a hepatitis C virus (HCV) infection comprising administering to a patient in need thereof a therapeutically effective amount of a combination of a compound of Formula I and a compound of Formula II.

The application provides a method for inhibiting replication of HCV in a cell comprising administering a combination of a compound of Formula I and a compound of Formula II.

Combination Therapy

The compounds of the invention and their isomeric forms and pharmaceutically acceptable salts thereof are useful in treating and preventing HCV infection alone or when used in combination with other compounds targeting viral or cellular elements or functions involved in the HCV lifecycle. Classes of compounds useful in the invention include, without limitation, all classes of HCV antivirals.

In particular, the cytidine nucleoside analogues of Formula I, in combination with the uridine nucleoside analogues of Formula II, produce a synergistic effect on the inhibition of HCV polymerase.

For combination therapies, mechanistic classes of agents that can be useful when combined with the compounds of the invention include, for example, nucleoside and non-nucleoside inhibitors of the HCV polymerase, protease inhibitors, helicase inhibitors, NS4B inhibitors and medicinal agents that functionally inhibit the internal ribosomal entry site (IRES) and other medicaments that inhibit HCV cell attachment or virus entry, HCV RNA translation, HCV RNA transcription, replication or HCV maturation, assembly or virus release. Specific compounds in these classes and useful in the invention include, but are not limited to, macrocyclic, heterocyclic and linear HCV protease inhibitors such as telaprevir (VX-950), boceprevir (SCH-503034), narlaprevir (SCH-9005 18), ITMN- 191 (R-7227), TMC-435350 (a.k.a. TMC-435), MK-7009, BI-201335, BI-2061 (ciluprevir), BMS-650032, ACH-1625, ACH-1095 (HCV NS4A protease co-factor inhibitor), VX-500, VX-8 13, PHX-1766, PHX2054, IDX- 136, IDX-3 16, ABT-450 EP-0 13420 (and congeners) and VBY-376; the Nucleosidic HCV polymerase (replicase) inhibitors useful in the invention include, but are not limited to, R7128, PSI-785 1, IDX-184, IDX-102, R1479, UNX-08 189, PSI-6130, PSI-938 and PSI-879 and various other nucleoside and nucleotide analogs and HCV inhibitors including (but not limited to) those derived as 2'-C-methyl modified nucleos(t)ides, 4'-aza modified nucleos(t)ides, and 7'-deaza modified nucleos(t)ides. Non-nucleosidic HCV polymerase (replicase) inhibitors useful in the invention, include, but are not limited to, HCV-796, HCV-371, VCH-759, VCH-916, VCH-222, ANA-598, MK-3281, ABT-333, ABT-072, PF-00868554, BI-207127, GS-9190, A-837093, JKT-109, GL-59728 and GL-60667.

In addition, compounds of the invention can be used in combination with cyclophyllin and immunophyllin antagonists (e.g., without limitation, DEBIO compounds, NM-811 as well as cyclosporine and its derivatives), kinase inhibitors, inhibitors of heat shock proteins (e.g., HSP90 and HSP70), other immunomodulatory agents that can include, without limitation, interferons (-alpha, -beta, -omega, -gamma, -lambda or synthetic) such as Intron A, Roferon-A, Canferon-A300, Advaferon, Infergen, Humoferon, Sumiferon MP, Alfaferone, IFN-β, Feron and the like; polyethylene glycol derivatized (pegylated) interferon compounds, such as PEG interferon-α-2a (Pegasys), PEG interferon-α-2b (PEGIntron), pegylated IFN-α-con1 and the like; long acting formulations and derivatizations of interferon compounds such as the albumin-fused interferon, Albuferon, Locteron, and the like; interferons with various types of controlled delivery systems (e.g., ITCA-638, omega-interferon delivered by the DUROS subcutaneous delivery system); compounds that stimulate the synthesis of interferon in cells, such as resiquimod and the like; interleukins; compounds that enhance the development of type 1 helper T cell response, such as SCV-07 and the like; TOLL-like receptor agonists such as CpG-10101 (actilon), isotorabine, ANA773 and the like; thymosin α-1; ANA-245 and ANA-246; histamine dihydrochloride; propagermanium; tetrachlorodecaoxide; ampligen; IMP-321; KRN-7000; antibodies, such as civacir, XTL-6865 and the like and prophylactic and therapeutic vaccines such as InnoVac C, HCV E1E2/MF59 and the like. In addition, any of the above-described methods involving administering an NS5A inhibitor, a Type I interferon receptor agonist (e.g., an IFN-α) and a Type II interferon receptor agonist (e.g., an IFN-γ) can be augmented by administration of an effective amount of a TNF-α antagonist. Exemplary, non-limiting TNF-α antagonists that are suitable for use in such combination therapies include ENBREL, REMICADE, and HUMIRA.

In addition, compounds of the invention can be used in combination with antiprotozoans and other antivirals thought to be effective in the treatment of HCV infection such as, without limitation, the prodrug nitazoxanide. Nitazoxanide can be used as an agent in combination with the compounds disclosed in this invention as well as in combination with other agents useful in treating HCV infection such as peginterferon α-2a and ribavirin.

Compounds of the invention can also be used with alternative forms of interferons and pegylated interferons, ribavirin or its analogs (e.g., tarabavarin, levoviron), microRNA, small interfering RNA compounds (e.g., SIR-PLEX-140-N and the like), nucleotide or nucleoside analogs, immunoglobulins, hepatoprotectants, anti-inflammatory agents and other inhibitors of NS5A. Inhibitors of other targets in the HCV lifecycle include NS3 helicase inhibitors; NS4A co-factor inhibitors; antisense oligonucleotide inhibitors, such as ISIS-14803, AVI-4065 and the like; vector-encoded short hairpin RNA (shRNA); HCV specific ribozymes such as heptazyme, RPI, 13919 and the like; entry inhibitors such as HepeX-C, HuMax-HepC and the like; alpha glucosidase inhibitors such as celgosivir, UT-231B and the like; KPE-02003002 and BIVN 401 and IMPDH inhibitors. Other illustrative HCV inhibitor compounds include those disclosed in the following publications: U.S. Pat. Nos. 5,807,876; 6,498,178; 6,344,465; and 6,054,472; PCT Patent Application Publication Nos. WO07/40028; WO98/4038 1; WO00/56331, WO02/04425; WO03/007945; WO03/010141; WO03/000254; WO01/32153; WO00/06529; WO00/18231; WO00/10573; WO00/13708; WO01/85172; WO03/037893; WO03/037894; WO03/037895; WO02/100851; WO02/100846; WO99/01582; WO00/09543; WO02/18369; WO98/17679, WO00/056331; WO98/22496; WO99/07734; WO05/073216, WO05/073195 and WO08/021927.

Additionally, combinations of, for example, ribavirin and interferon, may be administered as multiple combination therapy with at least one of the compounds of the invention. The present invention is not limited to the aforementioned classes or compounds and contemplates known and new compounds and combinations of biologically active agents. It is intended that combination therapies of the present invention include any chemically compatible combination of a compound of this inventive group with other compounds of the inventive group or other compounds outside of the inventive group, as long as the combination does not eliminate the anti-viral activity of the compound of this inventive group or the anti-viral activity of the pharmaceutical composition itself.

Combination therapy can be sequential, that is treatment with one agent first and then a second agent (for example, where each treatment comprises a different compound of the invention or where one treatment comprises a compound of the invention and the other comprises one or more biologically active agents) or it can be treatment with both agents at the same time (concurrently). Sequential therapy can include a reasonable time after the completion of the first therapy before beginning the second therapy. Treatment with both agents at the same time can be in the same daily dose or in separate doses. Combination therapy need not be limited to two agents and may include three or more agents. The dosages for both concurrent and sequential combination therapy will depend on absorption, distribution, metabolism and excretion rates of the components of the combination therapy as well as other factors known to one of skill in the art. Dosage values will also vary with the severity of the condition to be alleviated. It is to be further understood that for any particular subject, specific dosage regimens and schedules may be adjusted over time according to the individual's need and the judgment of the one skilled in the art administering or supervising the administration of the combination therapy.

The application provides a method for treating a hepatitis C virus (HCV) infection comprising administering to a patient in need thereof a therapeutically effective amount of a compound of any one of Formula I.

The application provides the above method, further comprising administering an immune system modulator or an antiviral agent that inhibits replication of HCV, or a combination thereof.

The application provides the above method, wherein the immune system modulator is an interferon or chemically derivatized interferon.

The application provides the above methods, wherein the antiviral agent is selected from the group consisting of a HCV protease inhibitor, a HCV polymerase inhibitor, a HCV helicase inhibitor, a HCV primase inhibitor, a HCV fusion inhibitor, and a combination thereof.

It will be understood that references herein to treatment extend to prophylaxis as well as to the treatment of existing conditions, and that the treatment of animals includes the treatment of humans as well as other mammals. Furthermore, treatment of an hepatitis C virus (HCV) infection, as used herein, also includes treatment or prophylaxis of a disease or a condition associated with or mediated by hepatitis C virus (HCV) infection, or the clinical symptoms thereof.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A compound of Formula I

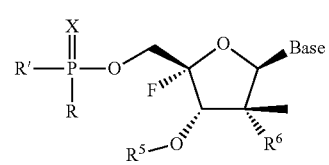

wherein:
R is O—$R^1$ or $NHR^{1'}$;
R' is $N(R^4)C(R^{2a})(R^{2b})C(=O)OR^3$ or —$OR^3$;
$R^1$ is H, lower haloalkyl, or aryl, wherein aryl is phenyl or naphthyl, optionally substituted with one or more lower alkyl, lower alkenyl, lower alkynyl, lower alkoxy, halo, lower haloalkyl, —$N(R^{1a})_2$, acylamino, —SO$_2$N(R$^{1a}$)$_2$, —COR$^{1b}$, —SO$_2$(R$^{1c}$), —NHSO$_2$(R$^{1c}$), nitro or cyano;

each R$^{1a}$ is independently H or lower alkyl;
each R$^{1b}$ is independently —OR$^{1a}$ or —N(R$^{1a}$)$_2$;
each R$^{1c}$ is lower alkyl;
R$^{1'}$ is —C(R$^{2a}$)(R$^{2b}$)C(=O)OR$^3$;
each R$^{2a}$ and R$^{2b}$ are independently H, lower alkyl, —(CH$_2$)$_r$N(R$^{1a}$)$_2$, lower hydroxyalkyl, —CH$_2$SH;
each R$^3$ is H, lower alkyl, lower haloalkyl, phenyl or phenyl lower alkyl;
each R$^4$ is H, lower alkyl;
R$^5$ is P(=O)(OR$^1$)(OR$^{1a}$), or P(=O)(OR$^1$)(NR$^4$R$^7$);
R$^6$ is OH or F;
R$^7$ is C(R$^{2a}$R$^{2b}$)C(=O) OR$^3$;
X is O or S; and
Base is guanine or adenine, each of which may optionally substituted with one or more hydroxy, lower alkyl, lower alkoxy, halo, nitro or cyano;
or a pharmacologically acceptable salt thereof.

2. The compound of claim 1, wherein R$^4$ is H.

3. The compound of claim 2, wherein R$^6$ is F.

4. The compound of claim 3, wherein R$^1$ is naphthyl or phenyl.

5. The compound of claim 4, wherein R$^{2a}$ is H.

6. The compound of claim 5, wherein R$^{2b}$ is methyl.

7. The compound of claim 6, wherein R$^3$ is isopropyl.

8. The compound of claim 1, wherein R$^6$ is OH.

9. The compound of claim 8, wherein R' is —OR$^3$ and R$^3$ is isopropyl.

10. The compound of claim 1, wherein X is S.

11. The compound of claim 1, wherein X is O.

12. The compound of claim 1, wherein Base is adenine.

13. The compound of claim 1, wherein Base is guanine.

14. A method for treating a Hepatitis C Virus (HCV) infection comprising administering to a patient in need thereof a therapeutically effective amount of a compound of claim 1.

15. A composition comprising the compound of claim 1, admixed with at least one carrier, diluent or excipient.

* * * * *